(12) United States Patent
Thiruvengadam et al.

(10) Patent No.: US 8,138,180 B2
(45) Date of Patent: Mar. 20, 2012

(54) EXO-SELECTIVE SYNTHESIS OF HIMBACINE ANALOGS

(75) Inventors: Tiruvettipuram K. Thiruvengadam, Kendall Park, NJ (US); Anantha Sudhakar, Fremont, CA (US); Ngiap Kie Lim, Somerset, NJ (US); Daw-long Kwok, Gillette, NJ (US); George G. Wu, Basking Ridge, NJ (US); Tao Wang, Springfield, NJ (US); Mingsheng Huang, Plainsboro, NJ (US); Michael D. Green, Willingboro, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 12/827,000

(22) Filed: Jun. 30, 2010

(65) Prior Publication Data

US 2010/0267947 A1    Oct. 21, 2010

Related U.S. Application Data

(62) Division of application No. 11/330,521, filed on Jan. 12, 2006, now Pat. No. 7,772,276.

(60) Provisional application No. 60/644,428, filed on Jan. 14, 2005.

(51) Int. Cl.
   *A61K 31/535* (2006.01)
(52) U.S. Cl. .................................... 514/229.8
(58) Field of Classification Search ............... 514/229.8
   See application file for complete search history.

(56) References Cited

U.S. PATENT DOCUMENTS

| | | | |
|---|---|---|---|
| 6,063,847 A | 5/2000 | Chackalamannil et al. | |
| 6,326,380 B1 | 12/2001 | Chackalamannil et al. | |
| 6,645,987 B2 | 11/2003 | Chackalamannil et al. | |
| 7,235,567 B2 | 6/2007 | Wu | |
| 7,304,078 B2 | 12/2007 | Chackalamannil et al. | |
| 7,541,471 B2 | 6/2009 | Thiruvengadam et al. | |
| 7,605,275 B2 | 10/2009 | Chen et al. | |
| 7,626,045 B2 | 12/2009 | Thiruvengadam et al. | |
| 2003/0216437 A1 | 11/2003 | Chackalamannil et al. | |
| 2004/0176418 A1 | 9/2004 | Thiruvengadam et al. | |
| 2006/0172397 A1 | 8/2006 | Li et al. | |
| 2006/1017318 | 8/2006 | Thiruvengadam et al. | |
| 2006/0247450 A1 | 11/2006 | Wu et al. | |
| 2008/0004449 A1 | 1/2008 | Yong et al. | |
| 2008/0009651 A1 | 1/2008 | Thiruvengadam et al. | |
| 2009/0281321 A1 | 11/2009 | Wu et al. | |

FOREIGN PATENT DOCUMENTS

WO    WO 99/26943    6/1999
WO    WO 03/089428 A1    10/2003

OTHER PUBLICATIONS

Tao, Beata, et. al.; "Nonenzymatic Kinetic Resolution of Propargylic Alcohols by a Planar-Chiral DMAP Derivative: Crystallographic Characterization of the Acylated Catalyst"; J. Am. Chem. Soc.; 1999; 121 (21); pp. 5091-5092.
International Search Report, PCT/US2006/001015; mailed Aug. 21, 2006, pp. 1-2 of 6 pages.
Chackalamannil, et al.; "Discovery of Potent Orally Active Thrombin Receptor (Protease Activated Receptor 1) Antagonists as Novel Antithrombotic Agents"; J. Med. Chem., Sep. 22, 2005; vol. 48, No. 19, pages 5884-5887, web published Aug. 24, 2005.
Clasby, M. C., et al.; "Discovery and Synthesis of a novel series of quinoline-based thrombin receptor (PAR-1) antagonists", Bioorganic & Medicinal Chemistry Letters, Mar. 15, 2006, vol. 16, No. 6, pp. 1544-1548, web published Dec. 27, 2005.
F. Z. Dorwald "Side Reactions in Organic Synthesis: A Guide to Successful Synthesis Design" 2005, Wiley-VCH Veriag GmbH & Co. KGaA, Weinheim.
Hawleys Condensed Chemical Dictionary 2001, Wiley and Sons, p. 566.

*Primary Examiner* — Janet Andres
*Assistant Examiner* — John Mabry
(74) *Attorney, Agent, or Firm* — Mark W. Russell

(57) ABSTRACT

This application discloses a novel process for the synthesis of himbacine analogs, as well as the compounds produced thereby. The synthesis proceeds by alternative routes including the cyclic ketal amide route, the chiral carbamate amide route, and the chiral carbamate ester route. The compounds produced thereby are useful as thrombin receptor antagonists. The chemistry disclosed herein is exemplified in the following synthesis sequence:

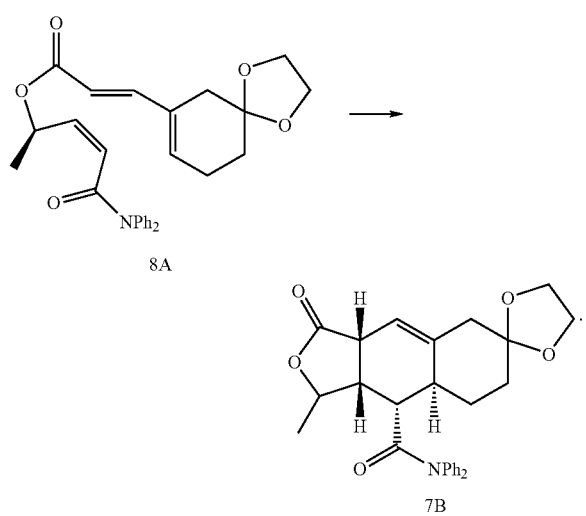

2 Claims, No Drawings

EXO-SELECTIVE SYNTHESIS OF HIMBACINE ANALOGS

This application is a divisional of application Ser. No. 11/330,521 filed Jan. 12, 2006, now allowed and herein incorporated by reference, which in turn claims the benefit of U.S. provisional application Ser. No. 60/644,428, filed Jan. 14, 2005.

FIELD OF THE INVENTION

This application discloses a novel process for the synthesis of himbacine analogs, as well as the analogs produced thereby. The synthesis proceeds by alternative routes including the cyclic ketal-amide route, the chiral carbamate-amide route, and the chiral carbamate-ester route. The compounds produced thereby are useful as thrombin receptor antagonists. The invention disclosed herein is related to those disclosed in the co-pending patent applications corresponding to U.S. provisional application Ser. Nos. 60/643,932; 60/643,927; and, 60/644,464, all four applications having been filed on the same date.

BACKGROUND OF THE INVENTION

Thrombin is known to have a variety of activities in different cell types and thrombin receptors are known to be present in such cell types as human platelets, vascular smooth muscle cells, endothelial cells, and fibroblasts. Thrombin receptor antagonists may be useful in the treatment of thrombotic, inflammatory, atherosclerotic and fibroproliferative disorders, as well as other disorders in which thrombin and its receptor play a pathological role. See, for example, U.S. Pat. No. 6,063,847, the disclosure of which is incorporated by reference.

One thrombin receptor antagonist is a compound of the formula and salts thereof:

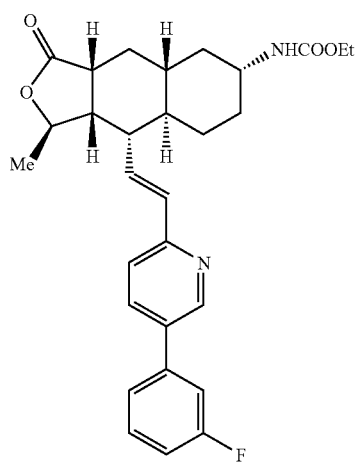

This compound is an orally bioavailable thrombin receptor antagonist derived from himbacine, and its synthesis proceeds through a Diels-Alder reaction.

Processes for the synthesis of similar himbacine analog thrombin receptor antagonists are disclosed in U.S. Pat. No. 6,063,847, and U.S. publication no. 2004/0216437A1; the synthesis of the bisulfate salt of a particular himbacine analog is disclosed in U.S. publication no. 2004/0176418A1, the disclosures of which are incorporated by reference herein.

The present invention provides an improved process for preparing thrombin receptor antagonists by providing at least one of a higher yield of the desired exo product via the Diels-Alder reaction, a simple and more efficient conversion of amide intermediates to their corresponding carboxylates, and improved purification of intermediates via crystallization.

SUMMARY OF THE INVENTION

In one embodiment, the present invention provides a process for preparing Compound 1:

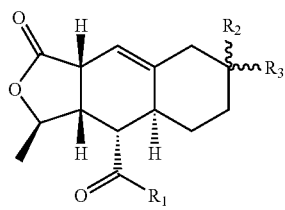

comprising cyclizing Compound 2:

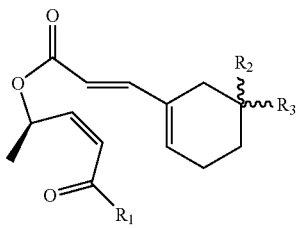

wherein $R_1$ is selected from the group consisting of $OR_4$ and $NR_5R_6$, $R_2$ and $R_3$ are independently selected from the group consisting of H, $NHR_7$, $OR_8$, $NHC(O)R_4$, and $NO_2$, or $R_2$ and $R_3$, taken together with the carbon to which they are attached, form a 5- to 7-membered heterocyclic ring containing 1 to 3 heteroatoms, and $R_4$, $R_5$, $R_6$, $R_7$, and $R_8$ are each independently selected from the group consisting of H, alkyl, alkoxy, cycloalkyl, aryl, alkylaryl, arylalkyl, and heteroaryl groups, or when $R_1$ is $NR_5R_6$ then $R_5$ and $R_6$ may, together with the nitrogen to which they are attached, form a 5- to 7-membered heterocyclic ring containing 1 to 3 heteroatoms.

In some embodiments, the solvent is selected from the group consisting of xylene, N-methylpyrrolidinone, Dimethylsulfoxide, diphenyl ether, Dimethylacetamide, and mixtures thereof.

In some embodiments, the base is selected from the group consisting of organic, inorganic, and organometallic bases.

In some embodiments, the base is selected from the group consisting of triethylamine, 1,5-diazabicyclo[4,3,0]non-5-ene, 1,4-diazabicyclo[2,2,2]octane, and 1,8-diazabicyclo[5,4,0]undec-7-ene.

In some embodiments, the temperature is between about 70° C. and about 190° C., preferably, between about 80° C. and about 170° C., more preferably, between about 100 and about 160° C., still more preferably, between about 120 and about 150° C.

In another embodiment, the present invention provides a process for preparing Compound 3:

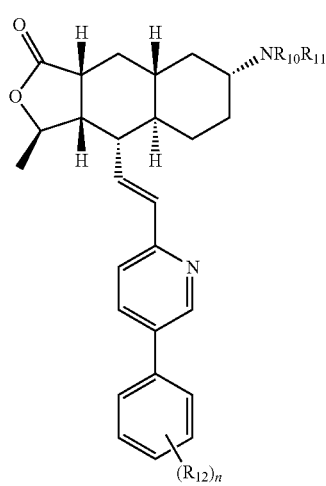

3 wherein $R_{10}$ and $R_{11}$ are each independently selected from the group consisting of H, alkyl, alkoxy, C(O)$R_4$, cycloalkyl, aryl, alkylaryl, arylalkyl, and heteroaryl groups, wherein $R_4$ is selected from the group consisting of H, alkyl, alkoxy, cycloalkyl, aryl, alkylaryl, arylalkyl, and heteroaryl groups, $R_{12}$ is selected from the group consisting of halogen, —$CF_3$, $C_1$-$C_6$ alkyl, $C_1$-$C_6$ alkoxy, and —COO$R_{13}$, wherein $R_{13}$ is selected from the group consisting of H, $C_1$-$C_6$ alkyl, phenyl, and benzyl, and n is an integer ranging from 1 to 5, comprising (a) reducing Compound 1 to Compound 4:

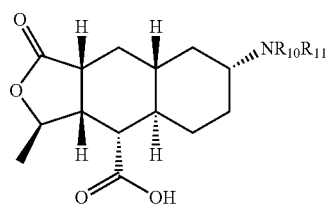

4

(b) converting Compound 4 to Compound 5:

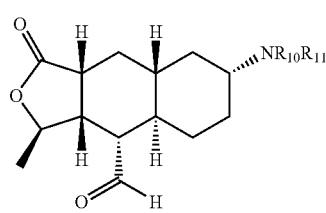

5

(c) converting Compound 5 to Compound 3 by reaction with Compound 6,

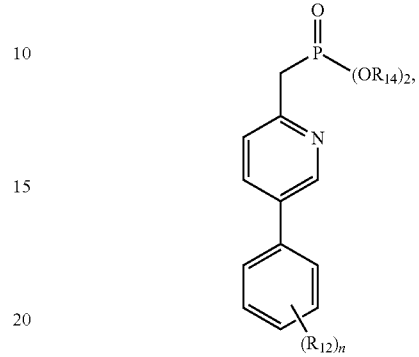

6 wherein $R_{14}$ is selected from the group consisting of alkyl, cycloalkyl, aryl, heteroaryl, and allyl.

In another embodiment, the present invention provides a process for preparing Compound 7:

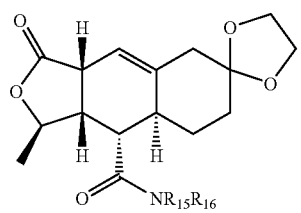

7 comprising cyclizing Compound 8:

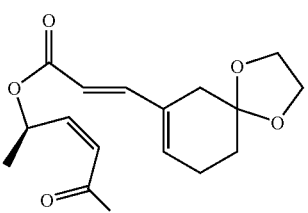

8 wherein $R_{15}$ and $R_{16}$ are each independently selected from the group consisting of H, alkyl, cycloalkyl, aryl, alkylaryl, arylalkyl, and heteroaryl groups or, when taken together with the nitrogen to which they are attached, may form a 3- to 6-membered heterocyclic ring containing 1 to 3 heteroatoms.

In another embodiment, the present invention provides a process for preparing Compound 3:

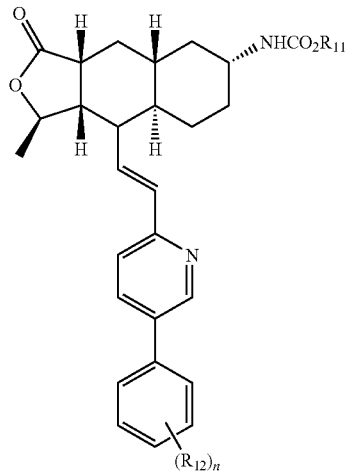

3A wherein $R_{11}$ and $R_{12}$ are as defined above, comprising:

(a) converting Compound 7 to Compound 14:

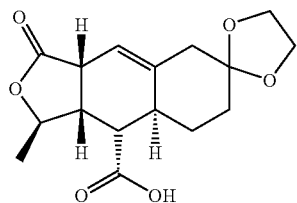

14

(b) reducing Compound 14, followed by hydrolysis, to yield Compound 15:

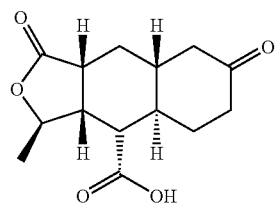

15

(c) aminating Compound 15 to yield Compound 4:

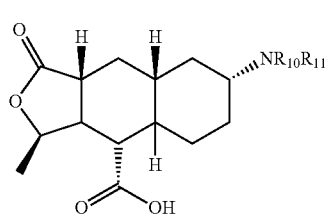

4 wherein $R_{10}$ and $R_{11}$ are as defined above;

(d) converting Compound 4 to Compound 17:

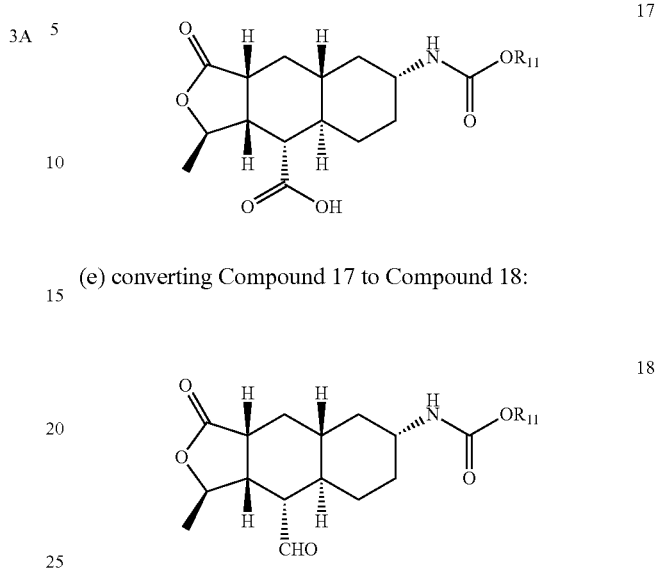

17

(e) converting Compound 17 to Compound 18:

18

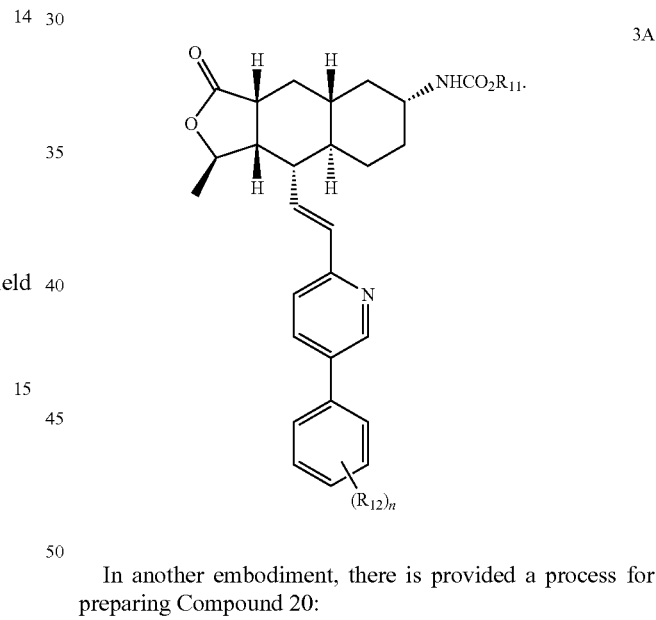

and (f) converting Compound 18 to Compound 3A:

3A

In another embodiment, there is provided a process for preparing Compound 20:

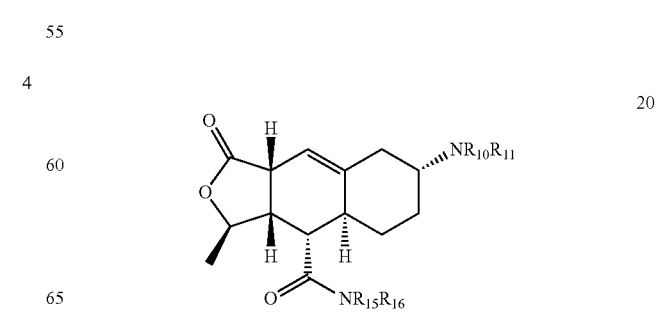

20 comprising cyclizing Compound 21:

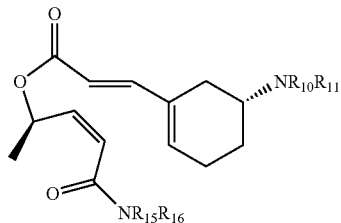

In another embodiment, there is provided a process for preparing Compound 3C:

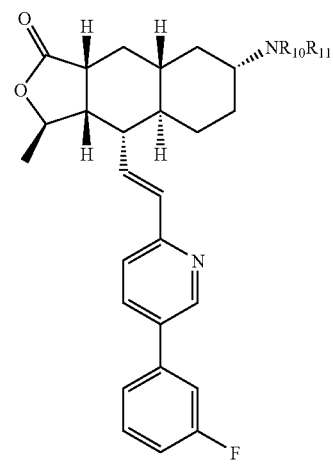

comprising:
(a) reducing Compound 24:

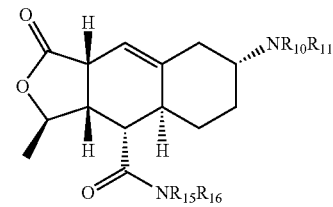

wherein $R_{10}$, $R_{11}$, $R_{15}$ and $R_{16}$ are as defined above, to yield Compound 25:

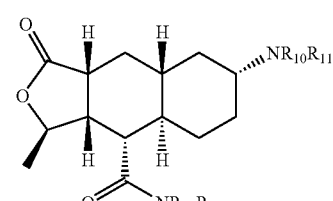

(b) converting Compound 25 to Compound 4:

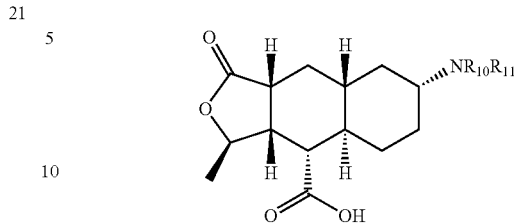

(c) converting Compound 4 to Compound 5:

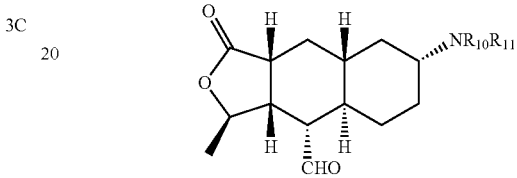

and (d) converting Compound 5 to Compound 3C:

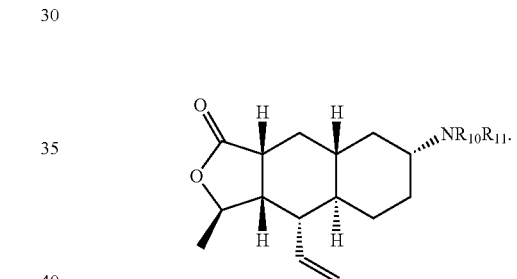

In yet another embodiment, there is provided a process for preparing Compound 27:

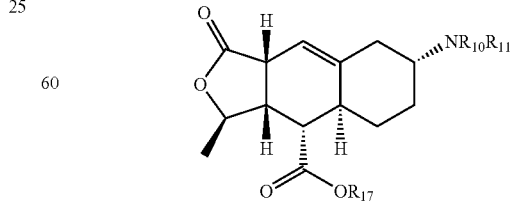

comprising cyclizing Compound 26:

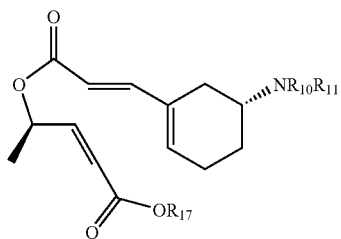

26

In another embodiment of the invention, there is provided a process for preparing Compound 3C:

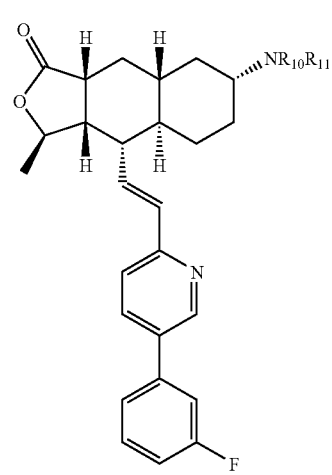

3C comprising:
(a) reducing Compound 27:

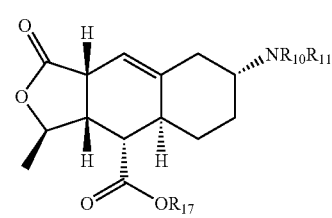

27 wherein $R_{10}$ and $R_{11}$ are as defined above, and $R_{17}$ is selected from the group consisting of H, alkyl, cycloalkyl, aryl, arylalkyl, and heteroaryl groups, to yield Compound 4:

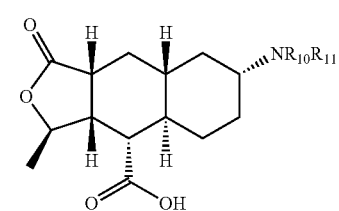

4

(d) converting Compound 4 to Compound 5:

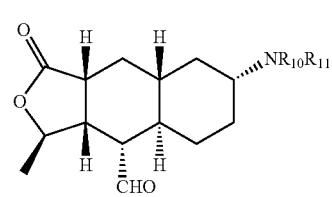

5

(e) converting Compound 5 to Compound 3C:

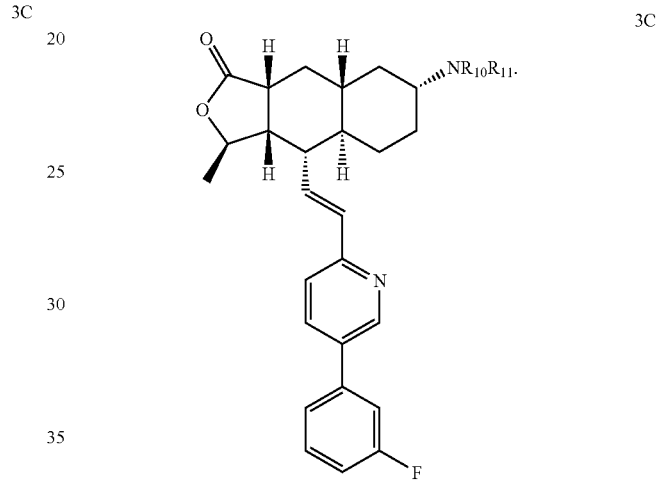

3C

In another embodiment of the present invention, there is provided a compound of the following formula:

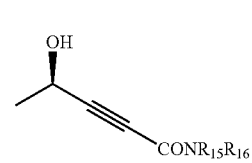

10 wherein $R_{15}$ and $R_{16}$ as defined above.

In still another embodiment of the present invention, there is provided a compound of the following formula:

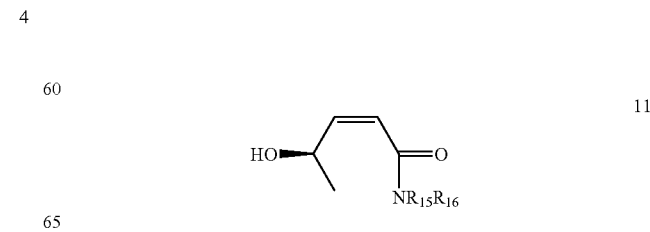

11 wherein $R_{15}$ and $R_{16}$ are as defined above.

In another embodiment of the present invention, there is provided a compound of the following formula:

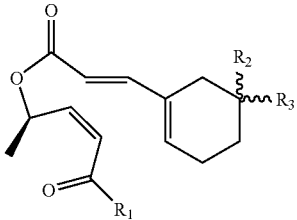

wherein $R_1$, $R_2$ and $R_3$ are as defined above.

In another embodiment of the present invention, there is provided a compound of the following formula:

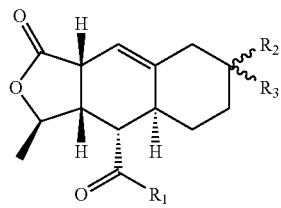

wherein $R_1$, $R_2$ and $R_3$ are as defined above.

In still another embodiment of the present invention, there is provided a compound of the following formula:

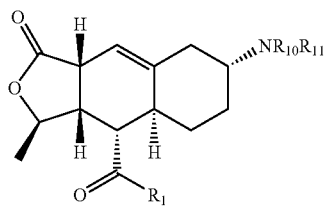

wherein $R_1$, $R_{10}$ and $R_{11}$ are as defined above.

In yet another embodiment, the present invention encompasses a compound of the following formula:

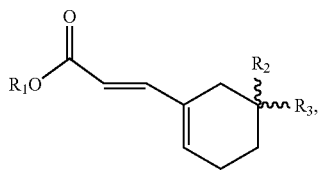

wherein $R_1$ is selected from the group consisting of H and $R_4$, and $R_2$ and $R_3$ are independently selected from the group consisting of H, $NHR_5$, $OR_6$, $NHC(O)R_7$, and $NO_2$, or $R_2$ and $R_3$, taken together with the carbon to which they are attached, form a 5- to 7-membered heterocyclic ring containing 1 to 3 heteroatoms, and $R_4$, $R_5$, $R_6$, and $R_7$ are each independently selected from the group consisting of H, alkyl, alkoxy, cycloalkyl, aryl, alkylaryl, arylalkyl, and heteroaryl groups.

In yet other embodiments, the invention is directed to a compound of the following formula:

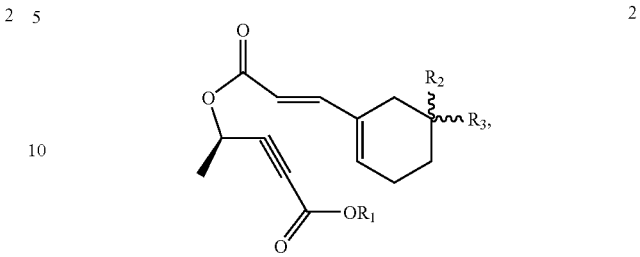

wherein $R_1$ is selected from the group consisting of $OR_4$ and $NR_5R_6$, $R_2$ and $R_3$ are independently selected from the group consisting of H, $NHR_7$, $OR_B$, $NHC(O)R_4$, and $NO_2$, or $R_2$ and $R_3$, taken together with the carbon to which they are attached, form a 5- to 7-membered heterocyclic ring containing 1 to 3 heteroatoms, and $R_4$, $R_5$, $R_6$, $R_7$, and $R_8$ are each independently selected from the group consisting of H, alkyl, alkoxy, cycloalkyl, aryl, alkylaryl, arylalkyl, and heteroaryl groups, or when $R_1$ is $NR_5R_6$ then $R_5$ and $R_6$ may, together with the nitrogen to which they are attached, form a 3- to 6-membered heterocyclic ring containing 1 to 3 heteroatoms.

A further understanding of the invention will be had from the following detailed description of the invention.

DESCRIPTION OF THE INVENTION

The following definitions and terms are used herein or are otherwise known to a skilled artisan. Except where stated otherwise, the definitions apply throughout the specification and claims. Chemical names, common names and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc.

Unless otherwise known, stated or shown to be to the contrary, the point of attachment for a multiple term substituent (two or more terms that are combined to identify a single moiety) to a subject structure is through the last named term of the multiple term substituent. For example, a cycloalkylalkyl substituent attaches to a targeted structure through the latter "alkyl" portion of the substituent (e.g., structure-alkyl-cycloalkyl).

The identity of each variable appearing more than once in a formula may be independently selected from the definition for that variable, unless otherwise indicated.

Unless stated, shown or otherwise known to be the contrary, all atoms illustrated in chemical formulas for covalent compounds possess normal valencies. Thus, hydrogen atoms, double bonds, triple bonds and ring structures need not be expressly depicted in a general chemical formula.

Double bonds, where appropriate, may be represented by the presence of parentheses around an atom in a chemical formula. For example, a carbonyl functionality, —CO—, may also be represented in a chemical formula by —C(O)—, or —C(=O)—. One skilled in the art will be able to determine the presence or absence of double (and triple bonds) in a covalently-bonded molecule. For instance, it is readily recognized that a carboxyl functionality may be represented by —COON, —C(O)OH, —C(=O)OH or —CO₂H.

The term "heteroatom," as used herein, means a nitrogen, sulfur or oxygen atom. Multiple heteroatoms in the same group may be the same or different.

As used herein, the term "alkyl" means an aliphatic hydrocarbon group that can be straight or branched and comprises 1 to about 24 carbon atoms in the chain. Preferred alkyl groups comprise 1 to about 15 carbon atoms in the chain. More preferred alkyl groups comprise 1 to about 6 carbon atoms in the chain. "Branched" means that one or more lower alkyl groups such as methyl, ethyl or propyl, are attached to a linear alkyl chain. The alkyl can be substituted by one or more substituents independently selected from the group consisting of halo, aryl, cycloalkyl, cyano, hydroxy, alkoxy, alkylthio, amino, —NH(alkyl), —NH(cycloalkyl), —N(alkyl)$_2$ (which alkyls can be the same or different), carboxy and —C(O)O-alkyl. Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkenyl" means an aliphatic hydrocarbon group (straight or branched carbon chain) comprising one or more double bonds in the chain and which can be conjugated or unconjugated. Useful alkenyl groups can comprise 2 to about 15 carbon atoms in the chain, preferably 2 to about 12 carbon atoms in the chain, and more preferably 2 to about 6 carbon atoms in the chain. The alkenyl group can be substituted by one or more substituents independently selected from the group consisting of halo, alkyl, aryl, cycloalkyl, cyano and alkoxy. Non-limiting examples of suitable alkenyl groups include ethenyl, propenyl, n-butenyl, 3-methylbut-enyl and n-pentenyl.

Where an alkyl or alkenyl chain joins two other variables and is therefore bivalent, the terms alkylene and alkenylene, respectively, are used.

"Alkoxy" means an alkyl-O— group in which the alkyl group is as previously described. Useful alkoxy groups can comprise 1 to about 12 carbon atoms, preferably 1 to about 6 carbon atoms. Non-limiting examples of suitable alkoxy groups include methoxy, ethoxy and isopropoxy. The alkyl group of the alkoxy is linked to an adjacent moiety through the ether oxygen.

The term "cycloalkyl" as used herein, means an unsubstituted or substituted, saturated, stable, non-aromatic, chemically-feasible carbocyclic ring having preferably from three to fifteen carbon atoms, more preferably, from three to eight carbon atoms. The cycloalkyl carbon ring radical is saturated and may be fused, for example, benzofused, with one to two cycloalkyl, aromatic, heterocyclic or heteroaromatic rings. The cycloalkyl may be attached at any endocyclic carbon atom that results in a stable structure. Preferred carbocyclic rings have from five to six carbons. Examples of cycloalkyl radicals include cyclopropyl, cyclobutyl, cyclopentyl, cyclohexyl, cycloheptyl, or the like.

"Alkynyl" means an aliphatic hydrocarbon group comprising at least one carbon-carbon triple bond and which may be straight or branched and comprising about 2 to about 15 carbon atoms in the chain. Preferred alkynyl groups have about 2 to about 10 carbon atoms in the chain; and more preferably about 2 to about 6 carbon atoms in the chain. Branched means that one or more lower alkyl groups such as methyl, ethyl or propyl, are attached to a linear alkynyl chain. Non-limiting examples of suitable alkynyl groups include ethynyl, propynyl, 2-butynyl, 3-methylbutynyl, n-pentynyl, and decynyl. The alkynyl group may be substituted by one or more substituents which may be the same or different, each substituent being independently selected from the group consisting of alkyl, aryl and cycloalkyl.

The term "aryl," as used herein, means a substituted or unsubstituted, aromatic, mono- or bicyclic, chemically-feasible carbocyclic ring system having from one to two aromatic rings. The aryl moiety will generally have from 6 to 14 carbon atoms with all available substitutable carbon atoms of the aryl moiety being intended as possible points of attachment. Representative examples include phenyl, tolyl, xylyl, cumenyl, naphthyl, tetrahydronaphthyl, indanyl, indenyl, or the like. If desired, the carbocyclic moiety can be substituted with from one to five, preferably, one to three, moieties, such as mono- through pentahalo, alkyl, trifluoromethyl, phenyl, hydroxy, alkoxy, phenoxy, amino, monoalkylamino, dialkylamino, or the like.

"Heteroaryl" means a monocyclic or multicyclic aromatic ring system of about 5 to about 14 ring atoms, preferably about 5 to about 10 ring atoms, in which one or more of the atoms in the ring system is/are atoms other than carbon, for example nitrogen, oxygen or sulfur. Mono- and polycyclic (e.g., bicyclic) heteroaryl groups can be unsubstituted or substituted with a plurality of substituents, preferably, one to five substituents, more preferably, one, two or three substituents (e.g., mono- through pentahalo, alkyl, trifluoromethyl, phenyl, hydroxy, alkoxy, phenoxy, amino, monoalkylamino, dialkylamino, or the like). Typically, a heteroaryl group represents a chemically-feasible cyclic group of five or six atoms, or a chemically-feasible bicyclic group of nine or ten atoms, at least one of which is carbon, and having at least one oxygen, sulfur or nitrogen atom interrupting a carbocyclic ring having a sufficient number of pi ($\pi$) electrons to provide aromatic character. Representative heteroaryl (heteroaromatic) groups are pyridinyl, pyrimidinyl, pyrazinyl, pyridazinyl, furanyl, benzofuranyl, thienyl, benzothienyl, thiazolyl, thiadiazolyl, imidazolyl, pyrazolyl, triazolyl, isothiazolyl, benzothiazolyl, benzoxazolyl, oxazolyl, pyrrolyl, isoxazolyl, 1,3,5-triazinyl and indolyl groups.

The term "heterocyclic ring" or "heterocycle," as used herein, means an unsubstituted or substituted, saturated, unsaturated or aromatic, chemically-feasible ring, comprised of carbon atoms and one or more heteroatoms in the ring. Heterocyclic rings may be monocyclic or polycyclic. Monocyclic rings preferably contain from three to eight atoms in the ring structure, more preferably, five to seven atoms. Polycyclic ring systems consisting of two rings preferably contain from six to sixteen atoms, most preferably, ten to twelve atoms. Polycyclic ring systems consisting of three rings contain preferably from thirteen to seventeen atoms, more preferably, fourteen or fifteen atoms. Each heterocyclic ring has at least one heteroatom. Unless otherwise stated, the heteroatoms may each be independently selected from the group consisting of nitrogen, sulfur and oxygen atoms.

The terms "Hal," "halo," "halogen" and "halide," as used herein, mean a chloro, bromo, fluoro or iodo atom radical. Chlorides, bromides and fluorides are preferred halides.

The following abbreviations are defined: ee is enantiomeric excess; EtOH is ethanol; Me is methyl; Et is ethyl; Bu is butyl; n-Bu is normal-butyl, t-Bu is tert-butyl, OAc is acetate; KOt-Bu is potassium tert-butoxide; NBS is N-bromo succinimide; NMP is 1-methyl-2-pyrrolidinone; DMA is N,N-dimethylacetamide; n-Bu$_4$NBr is tetrabutylammonium bromide; n-Bu$_4$NOH is tetrabutylammonium hydroxide, n-Bu$_4$NHSO$_4$ is tetrabutylammonium hydrogen sulfate, and equiv. is equivalents.

General Syntheses
The following general syntheses are illustrative of specific processes described in the examples that follow.
The following is a general scheme illustrating the cyclic ketal-amide route to the preparation of a himbacine analog:
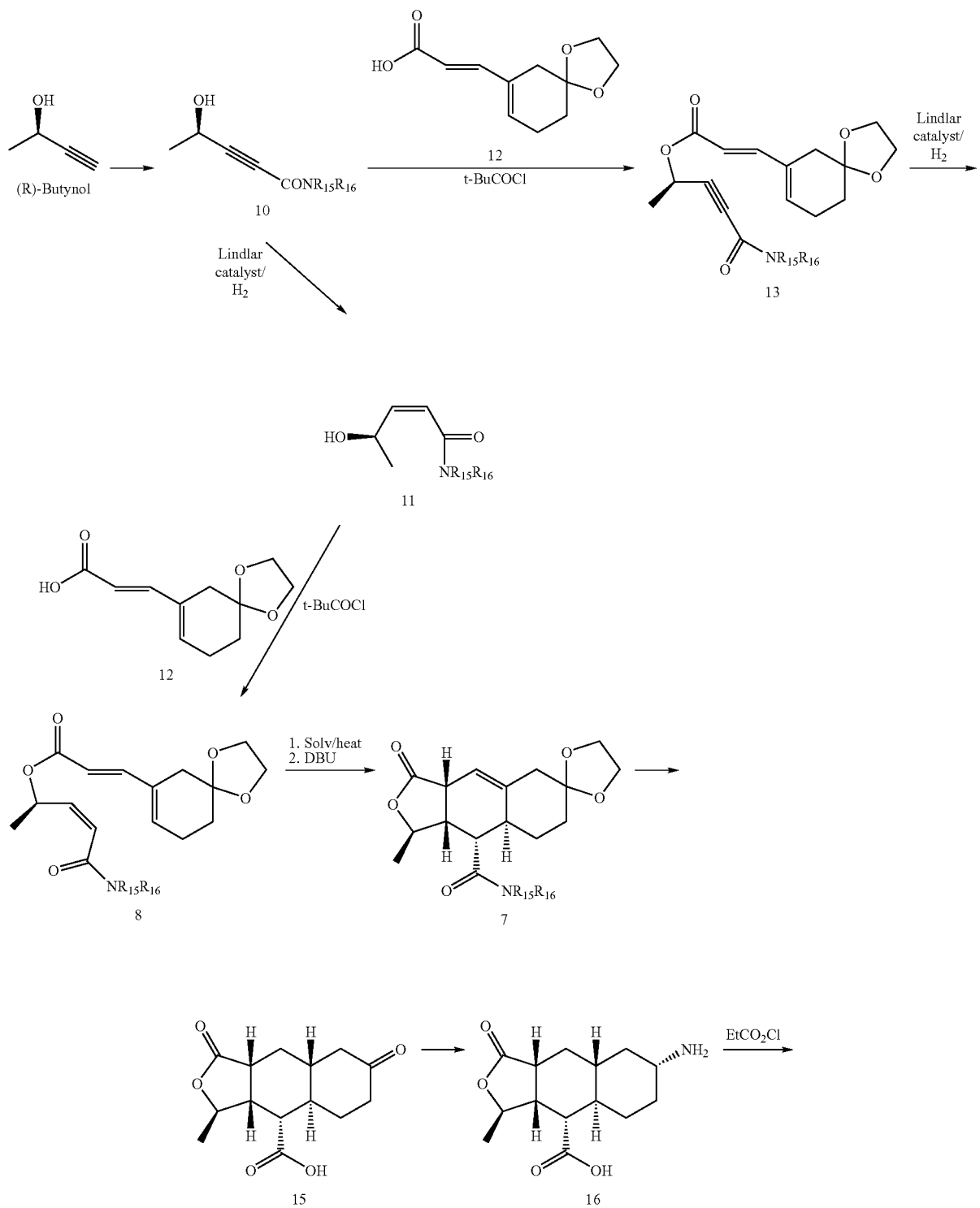

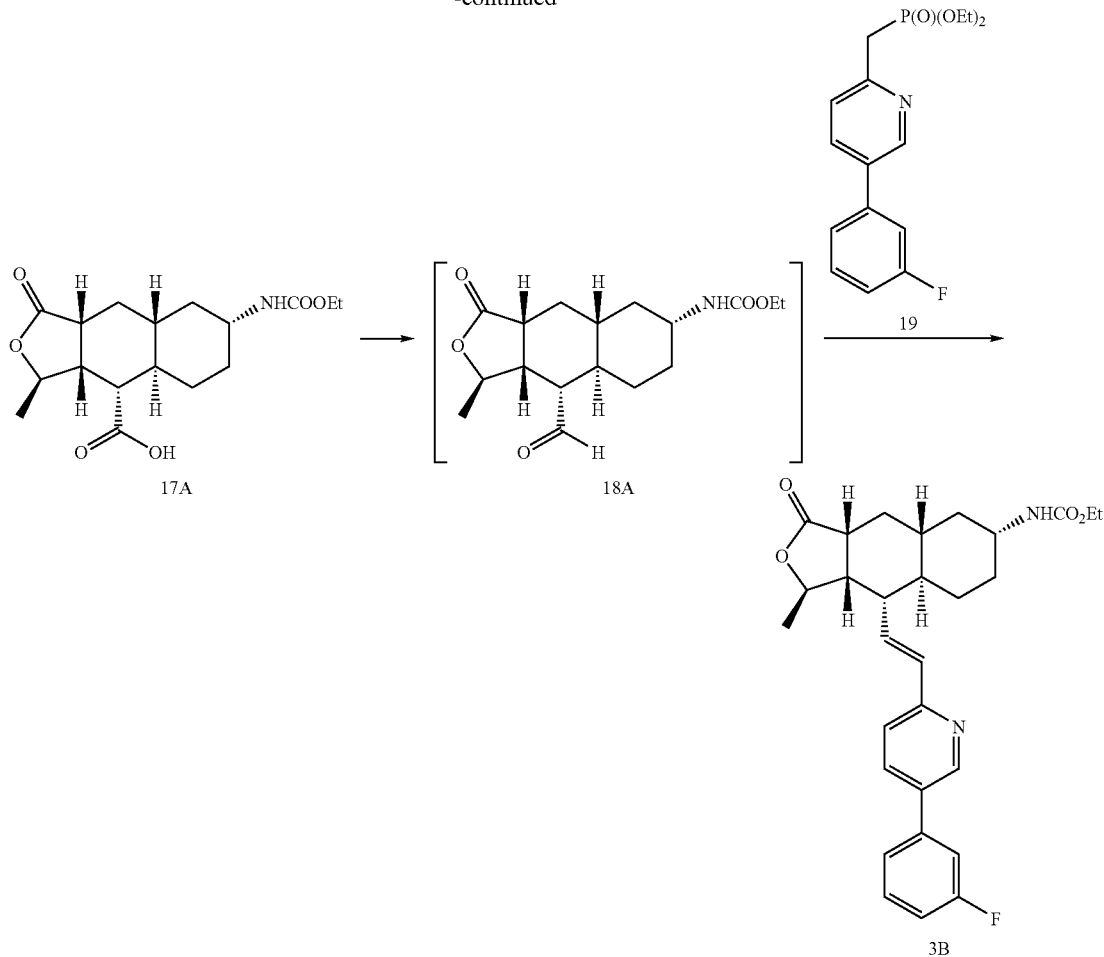
The butynol may be converted to amide 10 by a number of different methods, two of which are referred to as Method A and Method B:
Method A:
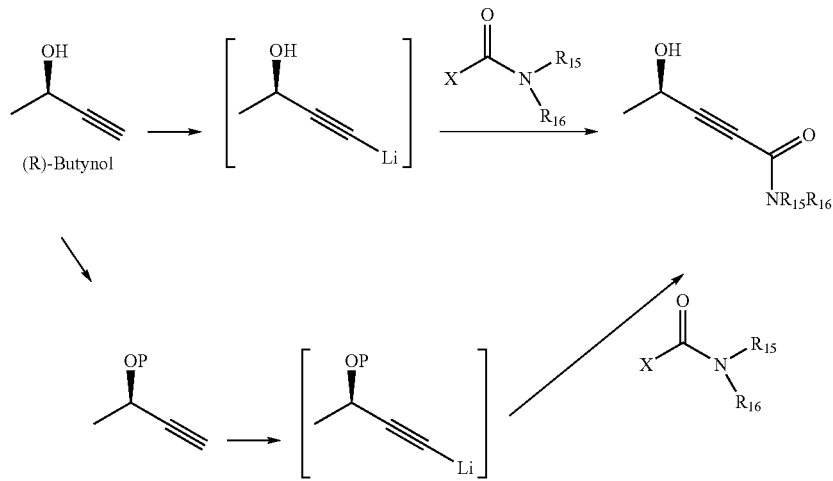
P = protecting group such as THP, SiR$^1$R$^2$R$^3$ Method B:

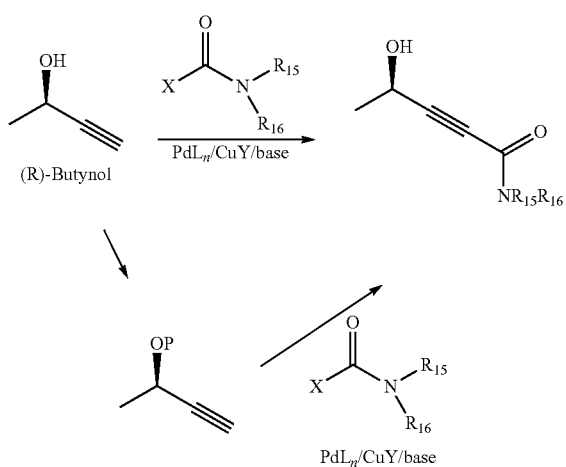

P = protecting group such as THP, SiR¹R²R³

In each of Methods A and B, P is a protecting group and X is a leaving group and is selected from the group consisting of Cl, Br, I, and heterocyclic rings, L is a ligand and is selected from $PR'_3$ wherein R' is selected from the group consisting of alkyl, aryl, alkylaryl, and NR'', wherein R'' is selected from the group consisting of alkyl, aryl, and alkylaryl, Y is selected from the group consisting of Cl, Br, I, and R'''COO, wherein R''' is selected from the group consisting of alkyl, aryl, alkylaryl, and arylalkyl, and n ranges from 0 to 4.

There are two alternative routes to Compound 8; in one route, amide 10 reacts with acid 12 to yield amide 13, which is subsequently reduced via Lindlar catalyst to amide 8. In the second route, amide 10 is reduced to vinyl alcohol 11, and a side chain is added by reaction with acid 12 to yield amide 8. Amide 8 is then cyclized via a Diels-Alder reaction condition in a suitable solvent (e.g., hydrocarbons such as xylene, N-methylpyrrolidinone, Dimethylsulfoxide, diphenyl ether, Dimethylacetamide and the like, as well mixtures thereof), at elevated temperature (e.g., from about 70° C. to about 190° C., preferably from about 80° C. to about 170° C., more preferably from about 100° C. to about 160° C., still more preferably from about 100° C. to about 150° C.), to produce a mixture of exo- and endo-isomers. This mixture is treated with a suitable base to complete the epimerization at the trans [5,6]-ring-junction to the cis-isomer (Compound 7). Suitable bases include, by way of non-limiting example, triethylamine, 1,5-diazabicyclo[4,3,0]non-5-ene, 1,4-diazabicyclo[2,2,2]octane, and 1,8-diazabicyclo[5,4,0]undec-7-ene. Compound 7 is subsequently reduced, for example, via hydrogenation, followed by hydrolysis to yield acid 15. The hydrogenation is preferably conducted in the presence of a hydrogenation catalyst, for example palladium on carbon.

Acid 15 is then subjected to amination conditions to yield amine 16. The amine is group is subsequently converted to the carbamate by reaction with an alkyl haloformate, for example ethyl chloroformate. The carbamate 17A is then converted to the corresponding aldehyde 18A, which is then reacted with phosphorus ester 19 to yield himbacine analog 3B.

Another route to himbacine analog 3B is the chiral carbamate-amide route, summarized as follows:

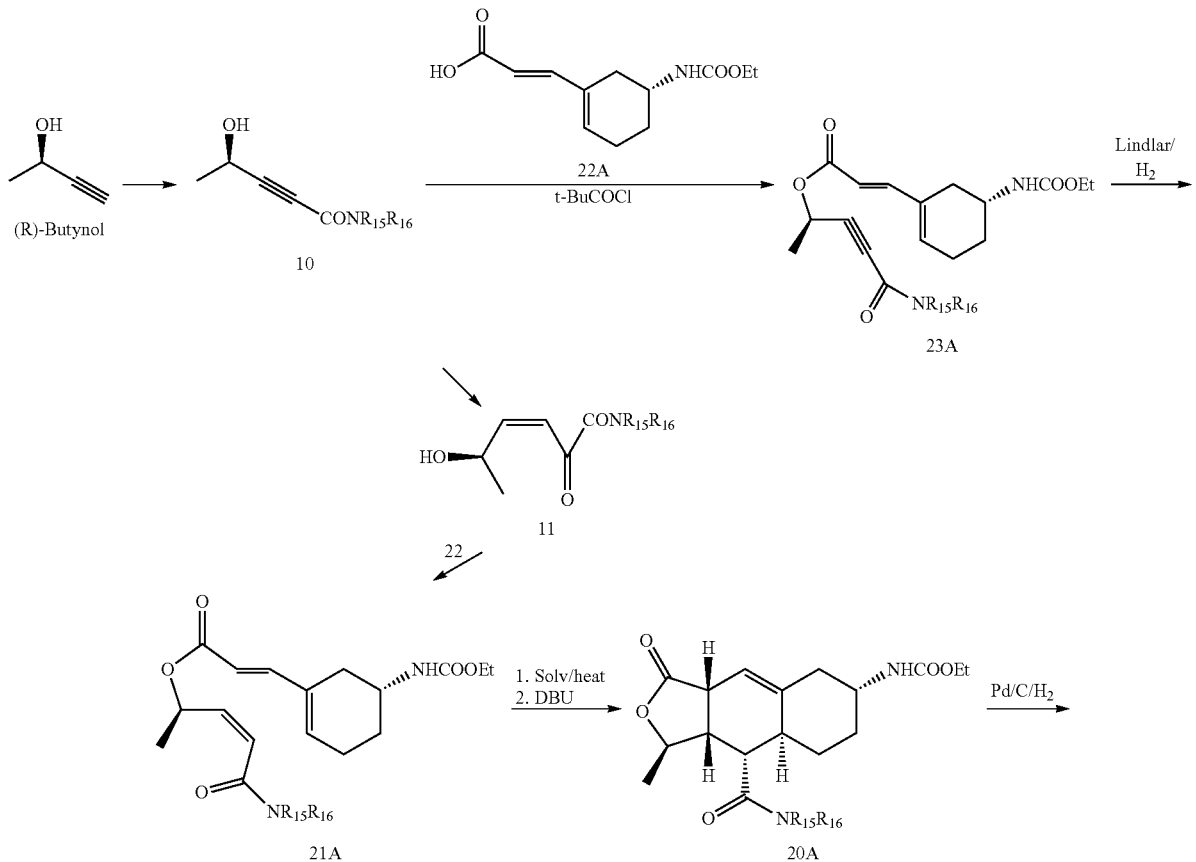

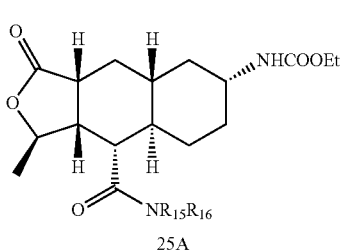

25A

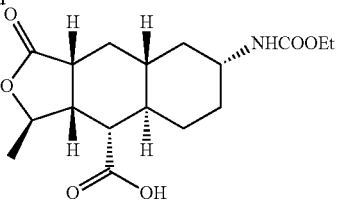

17A

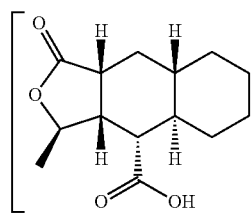

18A

19

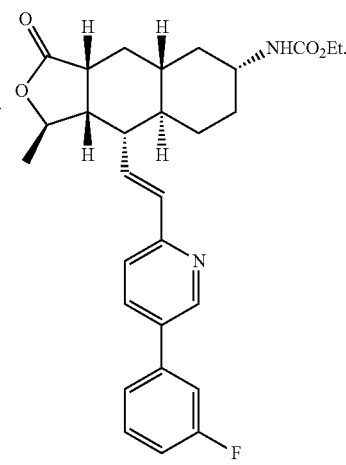

3B

In the chiral carbamate-amide route, amide 10 may be converted to carbamate-amide 21A via either of two routes. In the first route, amide 10 reacts with carbamate-acid 22A to yield amide 23A, which is subsequently reduced to carbamate-amide 21A. Carbamate-amide 21A is then cyclized via Diels-Alder reaction (as described above with respect to the cyclization and subsequent base treatment of Compound 8) to yield Compound 20A.

Carbamate-amide 20A is hydrogenated, preferably in the presence of a hydrogenation catalyst, to reduce the carbon-carbon double bond to yield Compound 25A. The amide 25A is converted to Compound 17A by reaction with a dilute solution of a strong base, followed by acidification with a mineral acid, for example hydrochloric acid. The carbamate acid 17A is then converted to the corresponding aldehyde 18A, which is then reacted with phosphate ester 19 to yield himbacine analog 3B.

Another route to a himbacine analog is via the chiral carbamate-ester route, and it is generally illustrated as follows:

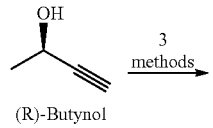

(R)-Butynol

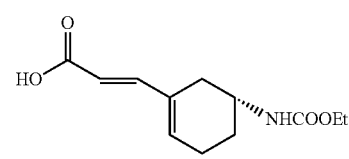

27A    22A

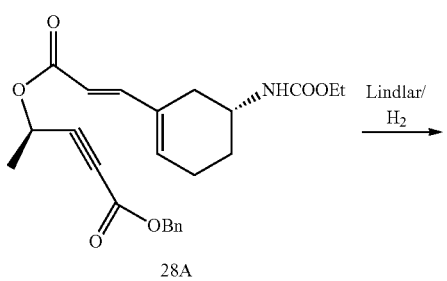

28A

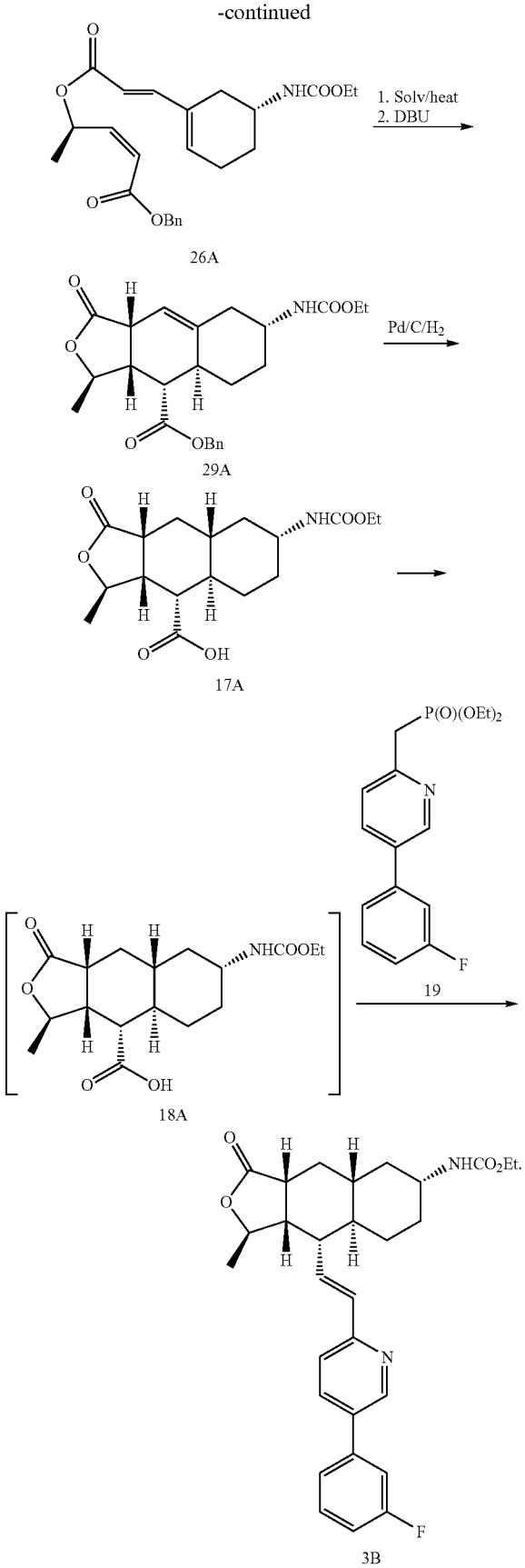

In this route, an ester 27A reacts with carbamate-acid 22A in the presence of trimethylacetyl chloride to yield 28A, which is subsequently reduced, preferably by hydrogen in the presence of Lindlar catalyst, to yield 26A. Compound 26A undergoes a Diels-Alder cyclization reaction (as described above with respect to the cyclization and subsequent base treatment of Compound 8) to yield 29A. Benzyl ester 29A is converted to the corresponding acid 17A by hydrogenation in the presence of one or more noble metal catalysts. Acid 17A is converted to the corresponding aldehyde 18A, which is then reacted with Compound 19 to yield himbacine analog 3B.

The experimental conditions disclosed herein are preferred conditions, and one of ordinary skill in the art can modify them as necessary to achieve the same products.

EXAMPLES

General. Unless otherwise specified, all reactions were performed under nitrogen atmosphere. 3-Butyn-2-ol, hexamethyldisilazane, copper iodide, triphenylphosphine, diphenylcarbamyl chloride, dimethylcarbamyl chloride, 4-morpholinecarbonyl chloride, diisopropylcarbamyl chloride, trimethylacetyl chloride, 4-(dimethylamino)pyridine, quinoline and 1,8-diazabicyclo[5.4.0]undec-7-ene were purchased from Aldrich. Lindlar's catalyst (5% $Pd/CaCO_3$ poisoned with Pb) was purchased from Johnson Matthey/Alfa Aesar, and platinum on carbon (5% Pt wt., 50% wet) from Engelhard. n-Butyllithium (2.5 M in hexane), triethylamine and bis(triphenylphosphine)palladium(II)chloride were purchased from Acros. (R)-3-Butyn-2-ol, and EDCl.HCl were purchased from commercial suppliers. Solvents and hydrogen gas (UHP grade) were purchased from commercial suppliers (Acros/Fisher and Airgas), and used without further purifications. NMR spectra were recorded on a Bruker 400 MHz spectrometer. HPLC analyses were performed on Waters 2690 Alliance equipped with Waters 996 Photodiode Array Detector.

| HPLC conditions: |||
|---|---|---|
| Column Waters Symmetry ® C-18 (3.9 × 150 mm) (WAT046980) |||
| Mobile phase Acetonitrile:Water with 0.1% trifluoroacetic acid (TFA) |||
| | Time (min) | % Acetonitrile | % Water with 0.1% TFA |
| Gradient program | 0 | 30 | 70 |
| | 14 | 30 | 70 |
| | 16 | 60 | 40 |
| | 25 | 60 | 40 |
| | 30 | 30 | 70 |
| Gradient program 2 | 0 | 45 | 55 |
| | 15 | 60 | 40 |
| | 25 | 45 | 55 |
| Isocratic program | 0 | 40 | 60 |
| | 30 | 40 | 60 |
| Detection | Waters 996 photodiode array detector |||

Example 1

Preparation of Amide-Method A

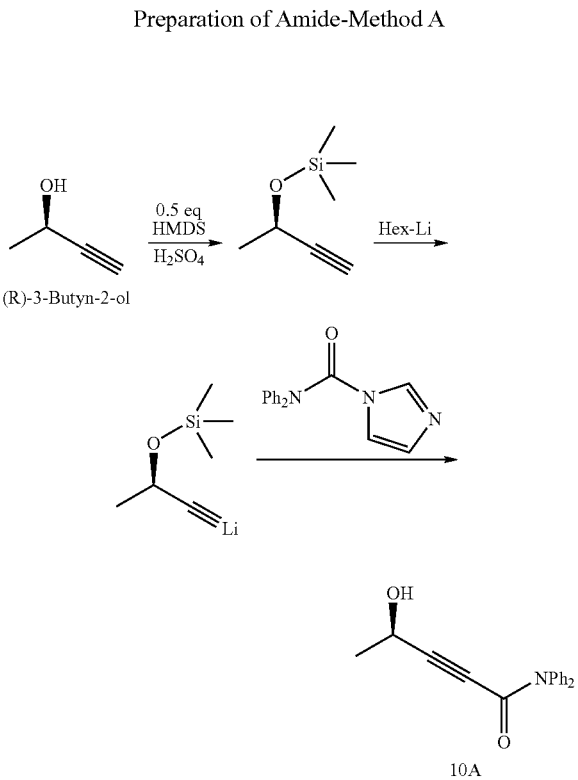

The following procedures can be operated on either the racemic or the enantiopure starting butyn-2-ol. To a stirred solution of sulfuric acid (conc., 40 µL) in THF (240 mL) were sequentially added (R)-3 butyn-2-ol (40 g, 0.57 mol) and then hexamethyldisilazane (49.6 g, 0.31 mol) at room temperature. The solution was refluxed for 3-4 hours and then slowly cooled to −40° C. The resulting mixture was slowly charged in hexyllithium (2.5M in hexane, 249 mL, 0.62 mol) while maintaining the temperature at −40° C. This solution and a solution of diphenylcarbamylimidazole (180 g, 0.68 mol) in a mixed solvent of THF (1088 mL) and toluene (435 mL) were mixed using pumps through a chilled static mixer and directly quenched into 5N sulfuric acid (560 mL, −5° C.). The quenched solution was warmed to 25° C. and stirred for 1 hour. The organic layer was separated, washed with 5N sulfuric acid (80 mL) and then twice with 10% brine (200 mL each time). The pH of the final brine wash was adjusted to 5-7 with a 5% NaHCO₃ solution. The organic layer was then distilled and replaced with toluene (440 mL). The toluene solution was added to heptane (400 mL) at 85° C., cooled slowly to 20° C. and filtered. The filtered cake was washed with a mixed solution of toluene (80 mL) and heptane (80 mL). The cake was then dried in a vacuum oven at 50° C. to afford the title compound in 84% molar yield (120.6 g, purity 99%). Mp 105° C. $^1$H NMR (400 MHz, DMSO-d$_6$) δ 1.04 (d, J=6.4 Hz, 3H), δ 4.27 (dq, J=5.6 Hz, 6.4 Hz, 1H), δ 5.49 (d, J=5.6 Hz, 1H), δ 7.2-7.5 (m, 10H); $^{13}$C NMR (DMSO-d$_6$) δ 23.7, 56.3, 76.9, 96.4, 126.8, 127.0, 128.5, 129.2, 129.4, 129.6, 141.5, 142.2, 152.9.

Example 2

Preparation of Dimethylamide 10B

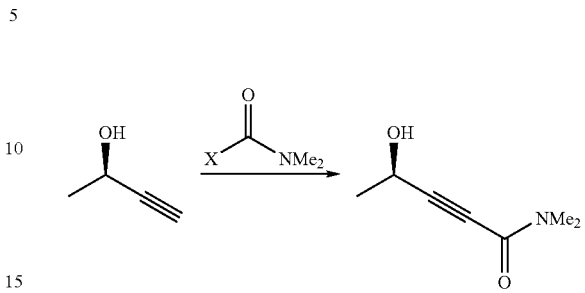

(1) Performed via Method A described above. In a procedure analogous to the synthesis of 10A above, the experiment performed gave 32.1% yield upon isolation by column chromatography.

$^1$H-NMR (CDCl$_3$, 400 MHz) □ 4.69 (m, 1H), 3.21 (s, 3H), 3.17 (d, 1H), 2.98 (s, 3H), 1.55 (d, 3H).

(2) Performed via Method B described below. In a procedure analogous to the synthesis of morpholine amide, the experiment performed gave 61.7% solution yield (by H-NMR assays) after 4 days at 55° C.

Example 3

Representative Procedures for Method B—Preparation of 4-Morpholine Amide

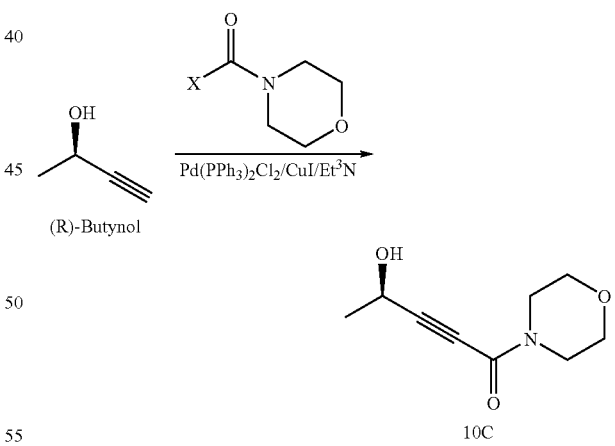

To 10 g (143 mmol) of (R)-3-butyne-2-ol was added 0.82 g (4.3 mmol) of CuI, 1.0 g (3.8 mmol) of PPh$_3$, 1.57 g of (2.23 mmol Pd(PPh$_3$)$_2$Cl$_2$), 21.34 g (143 mmol) of 4-morphorlinecarbonyl chloride, 100 mL of THF and 60 mL of triethylamine. The mixture was heated to 55° C. and maintained at this temperature for overnight. The solution was cooled to room temperature, filtered through celite and concentrated to an oil (32.0 g). The oil was purified through a SiO$_2$ column and crystallized from TBME to give 9.0 g of 10C as off-white crystals. $^1$H-NMR (CDCl$_3$, 400 MHz) □ 4.67 (q, 1H, J=6.6 Hz), 3.72 (m, 4H), 3.66 (m, 4H), 3.39 (m, 1H), 1.52 (d, 3H, J=6.6 Hz).

Example 4

Preparation of 10D Via Method A

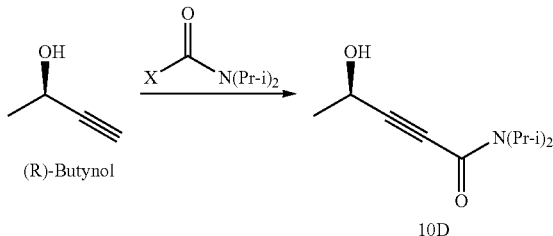

To 22 g (314 mmol) of (R)-3-butyne-2-ol is added 1.62 g (8.51 mmol) of CuI, 2.0 g (7.62 mmol) of PPh$_3$, 3.05 g of (4.33 mmol Pd(PPh$_3$)$_2$Cl$_2$), 46.7 g (285 mmol) of diisopropylcarbamoyl chloride, 200 mL of THF and 120 mL of triethylamine. The mixture is heated to 57° C. and maintained at this temperature overnight. The solution is cooled to room temperature, filtered through a pad of celite and concentrated to an oil. The purity of this oil is 42.6% and the yield is 48%. $^1$H-NMR (CDCl$_3$, 400 MHz) 14.65 (q, 1H, J=6.7 Hz), 4.55 (m, 1H), 4.16 (m, 1H), 3.60 (m, 1H), 1.50 (d, 3H, J=6.7 Hz), 1.35 (d, 6H, J=6.8 Hz), 1.23 (d, 6H, J=6.8 Hz).

Example 5

Preparation of 11 Via Lindlar Reduction

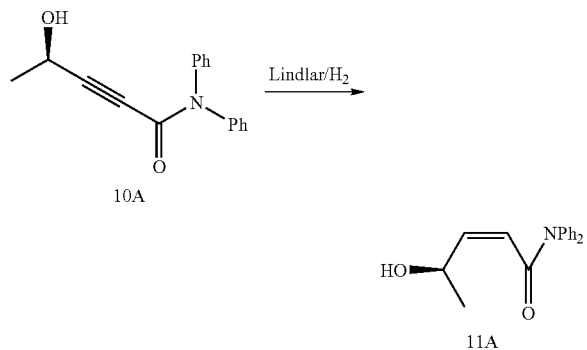

To a slurry of 10A (14.9 g, 56.2 mmol) and Lindlar's catalyst (5% Pd/CaCO$_3$, 0.50-0.75 g) in 200 mL of ethyl acetate was added hydrogen gas (1 atm, via balloon). The mixture was stirred at room temperature, and monitored at intervals for reaction progress by H-NMR. Upon completion of reaction, the mixture was filtered to remove catalysts, and concentrated on rotovap (35° C., 85 mbar) to give 16.0 g of brown oil. This crude cis-vinyl alcohol was used directly in subsequent synthesis step. $^1$H-NMR (CDCl$_3$, 400 MHz) □ 7.24-7.38 (m, 10H), 6.10 (q, 1H), 5.84 (dd, 1H), 4.88 (m, 1H), 4.59 (d, 1H), 1.36 (d, 3H).

Example 6

Preparation of 8A

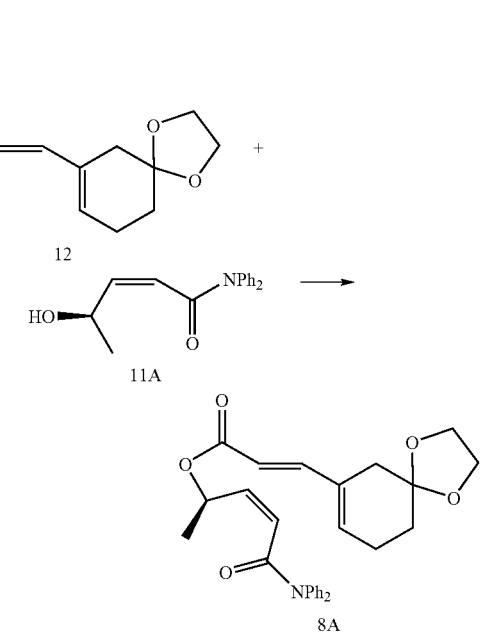

(1) Via mixed anhydride method. The coupling to the side chain acid was performed with 2.0 g of above material as follows: to a solution of 12 (2.4 g, 11.3 mmol) in 20 mL of THF was added triethylamine (3.7 mL, 26.3 mmol) at room temperature. The resulting brown solution was cooled to 0° C., and trimethylacetyl chloride (1.3 mL, 10.8 mmol) slowly added over 5 minutes. The mixture was stirred for 1 hour. 4-Dimethylaminopyridine (0.04 g, 0.3 mmol) and vinyl alcohol (2.0 g, 7.5 mmol) were then added. After 18 hours at 0° C., the mixture was warmed to room temperature, and quenched with 30 mL of water. Toluene (10 mL) was added to form a split. The upper organic layer was further washed with 40 mL of 2.5% ammonium hydroxide solution, and 30 mL of 10% sodium chloride solution before concentrating on rotovap (35° C., 50 mbar). Purification was performed on Biotage flash chromatography equipped with 90 g silica cartridge. After eluting with 1 L of 25% ethyl acetate/heptane and 0.5 L of 30% ethyl acetate/heptane, pure fractions were collected. Upon concentrating, 1.6 g of clear oil was obtained (49.9% yield). HPLC retention times (254 nm): 12, 1.9 min; 11A, 4.0 min; mixed anhydride, 9.4 min; 8A, 16.7 min. $^1$H-NMR (CDCl$_3$, 400 MHz) □ 7.37-7.45 (m, 11H), 6.37 (m, 1H), 6.26 (m, 1H), 5.84-5.96 (m, 3H), 4.08 (m, 4H), 2.49 (m, 4H), 1.88 (m, 2H), 1.58 (d, 3H).

(2) Via EDCl chemistry. To a slurry of 10A (25.0 g, 94.2 mmol) and Lindlar's catalyst (5% Pd/CaCO$_3$, 0.25-1.75 g) in 200 mL of ethyl acetate was added hydrogen gas (100 psi, Parr instrument). The mixture was stirred at room temperature, and monitored at intervals for reaction progress by H-NMR. Upon completion of reaction, the mixture was filtered to remove catalysts, washed forward with 30 mL of ethyl acetate and concentrated on rotovap (25° C., 35 mbar) to give 25.8 g of brown oil. This crude cis-vinyl alcohol intermediate was used directly in the subsequent synthesis step.

The coupling to the side chain acid was performed as follows: to a solution of cis-vinyl alcohol, 11A (23.8 g, 113 mmol) and 4-dimethylaminopyridine (5.8 g, 47 mmol) in 250 mL of methylene chloride was added EDCl.HCl (21.7 g, 113 mmol) at 0° C. The mixture was then stirred for 17 hours at 0° C., following which HPLC analysis showed <0.5% of alkenol remaining. The mixture was warmed to room temperature, and quenched with 200 mL of 1N sulfuric acid. The upper organic layer was washed with a mixture of 50 mL of saturated sodium bicarbonate solution and 50 mL of water to adjust the pH to 8. Upon concentrating, 58.1 g of dark brown oil was obtained. Purification was performed on Biotage Flash 75 chromatography equipped with 800 g silica cartridge. The crude product was loaded directly onto the column as oil, and further washed down with 2×20 mL of toluene. Pure fractions were collected after eluting with 10 L of 25% ethyl acetate/heptane. Upon concentrating, 21.6 g of pale yellow oil was obtained (49.9% yield).

Example 7

Diels-Alder Reaction

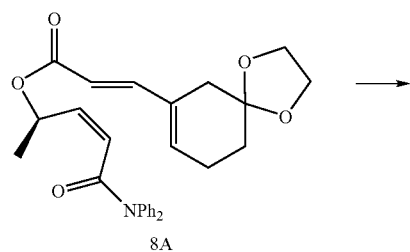

8A

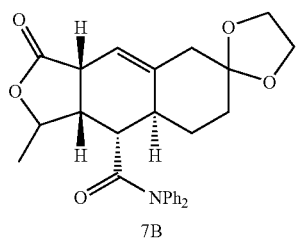

7B

Diels-Alder cyclization to 7B. A solution of 8A (21.6 g, 47.0 mmol) in 130 mL of o-xylene was heated at reflux (147° C.) for 16 hours, after which it was cooled to 40° C., and 1,8-diazabicyclo[5.40]undec-7-ene (DBU) (0.30 g, 1.9 mmol) was added. H-NMR analysis after 2 hours showed epimerization was complete, and a ratio of 94:6 for the exo/endo isomer. Heating was stopped, and the solution washed with 50 mL of 1N sulfuric acid to purge 1,8-diazabicyclo[5.40]undec-7-ene. A second wash with 50 mL of saturated sodium bicarbonate solution adjusted pH back to neutral. The organic layer was concentrated on rotovap (55° C., 25 mbar) to give 36 g of brown oil, which was loaded onto 800 g silica cartridge of Biotage Flash 75 chromatography and washed down with 2×20 mL of o-xylene. Pure fractions were obtained after eluting with 15 L of 40% ethyl acetate/heptane. Upon concentration, 18.6 g of white solid was obtained (86.1% yield). $^1$H-NMR (CDCl$_3$, 400 MHz) δ 7.23-7.47 (m, 10H), 5.29 (s, 1H), 4.73 (m, 1H), 3.98 (m, 4H), 3.02 (d, 1H), 2.76 (m, 2H), 2.49 (m, 1H), 2.40 (m, 2H), 2.11 (m, 1H), 1.84 (m, 1H), 1.76 (m, 1H), 1.56 (d, 3H), 1.24 (m, 1H).

Example 8

Preparation of 7C

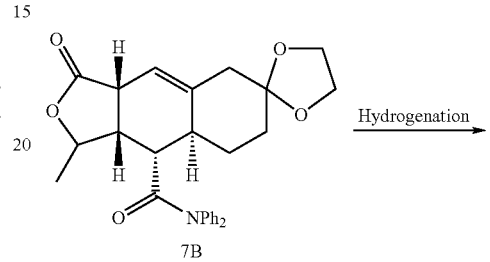

7B

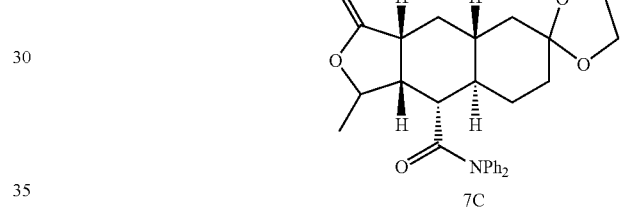

7C

To a slurry of 7B (18.6 g, 40.5 mmol) and 5% Pt on carbon (9.3-18.6 g) in 110 mL of ethyl acetate was added hydrogen gas (100 psi, via Parr instrument). The mixture was stirred at room temperature, and monitored at intervals for reaction progress by HPLC. After 37 hours, $^1$H-NMR showed approximately 10% of 7B left. The mixture was filtered to remove catalysts, washed forward with 100 mL of ethyl acetate and concentrated on rotovap (30° C., 40 mbar) to give 19.3 g of clear oil. A portion of this (17.6 g) was re-dissolved in 110 mL of ethyl acetate, and re-subjected to hydrogenation by adding 5% Pt on carbon (9.3 g) and hydrogen gas (100 psi, via Parr instrument). HPLC analysis after 24 hours showed the reaction was completed. The mixture was filtered, and washed forward with 50 mL of ethyl acetate and concentrated on rotovap (30° C., 60 mbar) to give 20.6 g of clear oil. Upon standing overnight, crystals were formed. Further sonication (for 2 minutes) and concentration (30° C., 30 mbar) gave 17.9 of white solid. A portion of the crude material (2.0 g) was re-dissolved in 5 mL of methylene chloride, loaded onto 90 g silica cartridge of Biotage flash chromatography and washed down with 2×5 mL of methylene chloride. Pure fractions were collected after eluting with 2 L of 45% ethyl acetate/heptane. Upon concentration on rotovap (30° C., 60 mbar), a white solid (1.5 g) was obtained (78.7% yield). HPLC retention times (254 nm): 7B, 7.4 min; 7C, 6.8 min. $^1$H-NMR (CDCl$_3$, 400 MHz) δ 7.23-7.56 (m, 10H), 4.92 (m, 1H), 3.93

(m, 4H), 2.54 (m, 1H), 2.31 (m, 1H), 2.02 (m, 1H), 1.81 (m, 2H), 1.69 (m, 3H), 1.56 (d, 3H), 1.29 (m, 4H).

Example 9

Preparation of 15

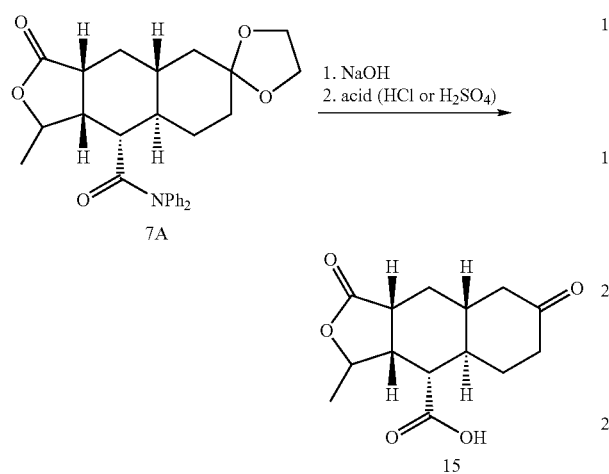

50 mg. of Compound 7A was mixed with 2 mL of 20% NaOH solution aq., and the mixture was stirred at room temperature for 16 hours. To this mixture was added 2.5 mL of 50% aq. HCl, and agitation continued for another 30 min. Compound 15 was extracted with TBME (4 mL) and the structure was confirmed by NMR.

Example 10

Preparation of 8A

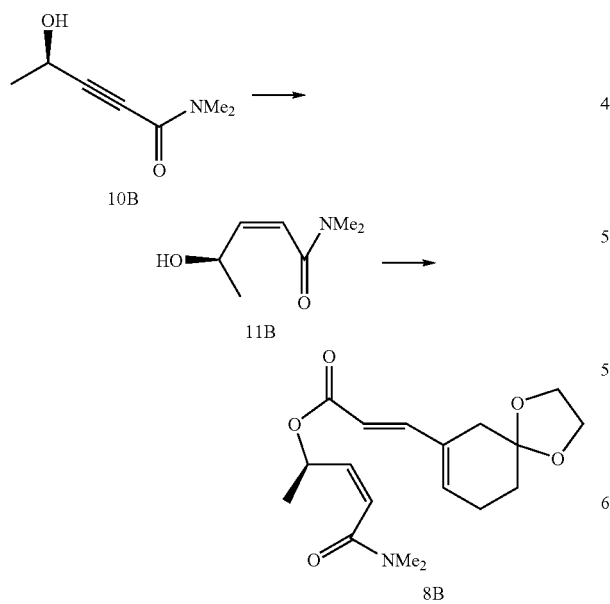

In a procedure analogous to the synthesis of ester 8A above via mixed anhydride chemistry, the experiment performed on 12 (1.0 g, 7.1 mmol) and Compound 11B gave 1.3 g of ester 8B (clear yellow oil, 54.9% yield). $^1$H-NMR of vinyl alcohol intermediate (CDCl$_3$, 400 MHz): 6.13 (m, 2H), 4.88 (d, 1H), 4.64 (m, 1H), 3.08 (s, 3H), 3.02 (s, 3H), 1.36 (d, 3H).

Example 11

Preparation of 7C

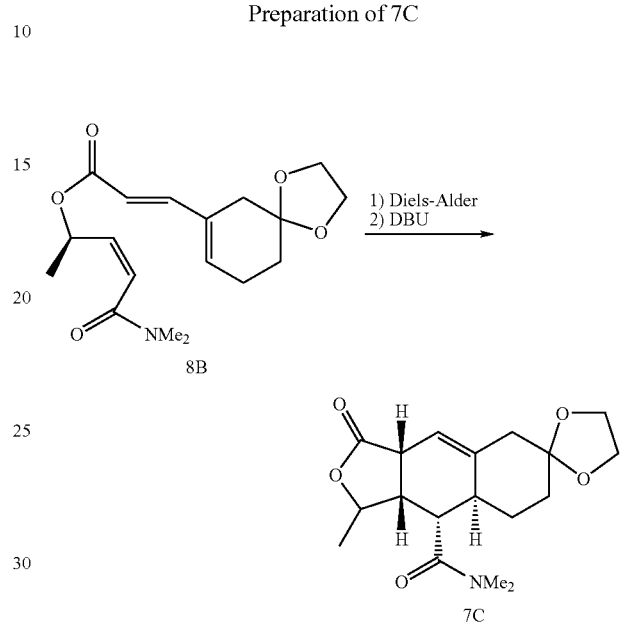

Diels-Alder cyclization to 7C. In a procedure analogous to the synthesis of 7B, the experiment performed on 8B (0.30 g, 0.89 mmol) showed 90:10 ratio of exo/endo isomer by H-NMR. $^1$H-NMR (CDCl$_3$, 400 MHz) □ 5.36 (s, 1H), 4.58 (m, 1H), 3.94 (m, 4H), 3.31 (m, 1H), 3.08 (s, 3H), 2.98 (s, 3H), 2.81 (m, 1H), 2.67 (m, 1H), 2.45 (m, 1H), 2.39 (s, 2H), 1.83 (m, 1H), 1.75 (m, 2H), 1.26 (d, 3H), 1.12 (m, 1H).

Example 12

Preparation of 13B

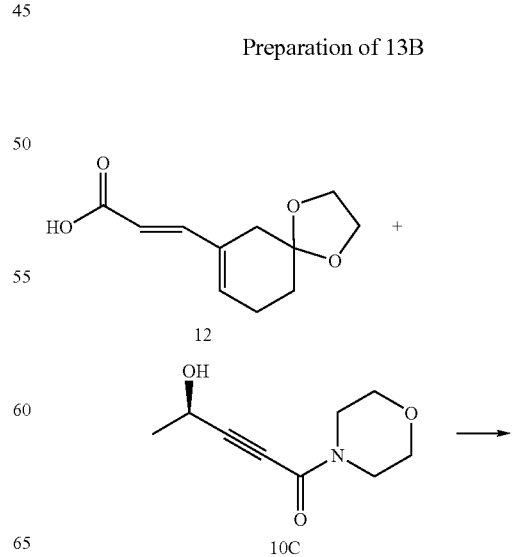

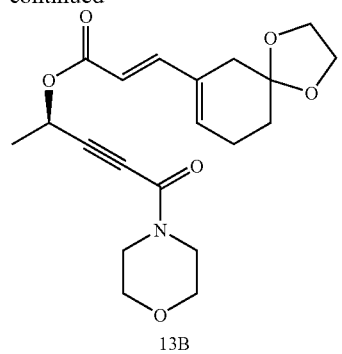

13B

In a procedure analogous to the synthesis of 8A, the experiment performed on alkynol amide 10C (5.4 g, 29.5 mmol) gave 8.2 g of yellow oil (73.9% yield after subtracting toluene solvent). HPLC retention times (gradient program 2, 254 nm): 12, 1.9 min; 13B, 3.6 min; mixed anhydride, 9.3 min. $^1$H-NMR (CDCl$_3$, 400 MHz) □ 7.41 (d, 1H), 6.25 (m, 1H), 5.76 (d, 1H), 5.63 (q, 1H), 4.01 (m, 4H), 3.72 (m, 4H), 3.68 (m, 4H), 2.48 (d, 2H), 2.40 (s, 2H), 1.80 (t, 2H), 1.59 (d, 3H).

Example 13

Preparation of 8B

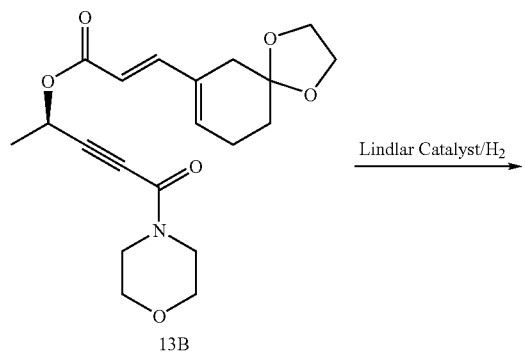

To a slurry of 13B (3.9 g, 10.4 mmol), quinoline (0.37 mL, 3.0 mmol) and Lindlar's catalyst (5% Pd/CaCO$_3$, 0.34-0.85 g) in 20 mL of toluene was added hydrogen gas (1 atm, via balloon). The mixture was stirred at room temperature, and monitored at intervals for reaction progress by HPLC. Upon completion of reaction (<4% of 13B on HPLC analysis), the mixture was filtered to remove catalysts, and 2×15 mL of toluene was used to rinse remaining materials forward. The filtrate was washed twice with 15 mL of 0.5 N hydrochloric acid solution (to purge quinoline), and then neutralized by further washing with 15 mL of saturated sodium bicarbonate solution and 15 mL of water. The isolated organic layer was concentrated on rotovap (40° C., 26 mm Hg) to give 3.7 g of clear oil (94.2% yield). HPLC retention times (gradient program, 254 nm): 8C, 8.5 min; 13B 14.1 min. $^1$H-NMR (CDCl$_3$, 400 MHz) □ 7.36 (d, 1H), 6.19 (m, 1H), 6.07 (d, 1H), 5.87 (m, 2H), 5.74 (d, 1H), 4.01 (m, 4H), 3.82 (m, 1H), 3.72 (m, 4H), 3.53 (m, 3H), 2.46 (d, 2H), 2.39 (s, 2H), 1.79 (t, 2H), 1.46 (d, 3H).

Example 14

Preparation of 7C Via Diels-Alder Reaction

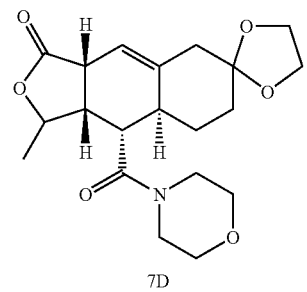

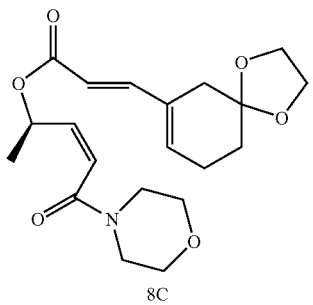

In a procedure analogous to the synthesis of 7, the experiment performed on 8C (3.4 g, 9.0 mmoL) showed an exo/endo ratio of 91:9 after epimerization by H-NMR. Upon purification via Biotage flash chromatography, 2.9 g of clear oil was obtained (85.2% yield). $^1$H-NMR (CDCl$_3$, 400 MHz) □ 5.36 (s, 1H), 4.59 (m, 1H), 3.96 (m, 5H), 3.60-3.72 (m, 7H), 3.52 (m, 2H), 3.37 (d, 1H), 2.75 (m, 2H), 2.40 (s, 1H), 2.37 (m, 1H), 1.89 (m, 1H), 1.76 (m, 2H), 1.30 (d, 3H), 1.13 (m, 1H).

Compound 7D was reduced following similar procedures described for the conversion of 7B to 7C.

Example 15

Preparation 13C

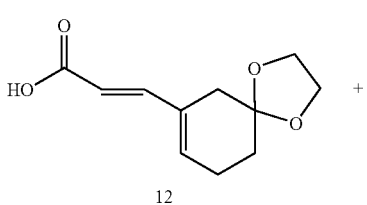

12

-continued

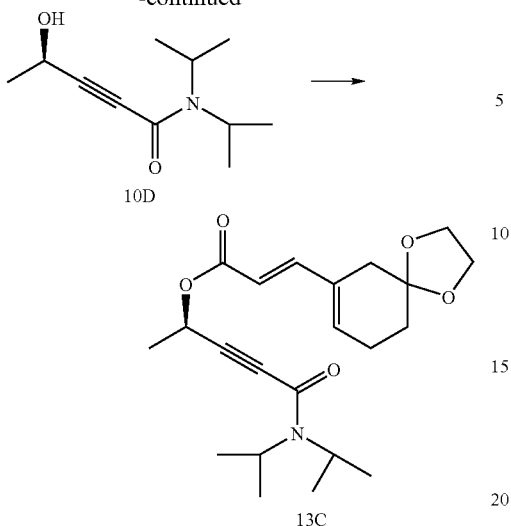

To a solution of 12 (16.6 g, 79 mmol) in 100 mL of toluene was added triethylamine (251 mL, 185 mmol), and the resulting slurry was cooled to 0° C. Mixed anhydride formation was initiated via addition of trimethylacetyl chloride (9.4 mL, 76 mmol) made slowly over 10 minutes, and completed through stirring at 0° C. for 30 minutes. Catalytic amounts of 4-(dimethylamino)pyridine (0.26 g, 2 mmol) and alcohol 10D (10.4 g, 53 mmol) were then added into the mixture, followed by 100 mL of tetrahydrofuran to wash remaining reagents down. After stirring for 18 hours at 0° C., cooling was removed, and the reaction mixture concentrated on rotovap (30° C., 26 mm Hg) to yield 73 g of brown oil.

Purification was performed on Biotage flash chromatograph equipped with 800 g silica cartridge. The crude material was made into a slurry with 25 mL of heptane, loaded onto the column, and washed down with methylene chloride (10 mL). Pure fractions were collected after eluting with 10 L of 25% ethyl acetate in heptane and 5 L of 20% ethyl acetate in heptane. Upon concentrating, Compound 13C was obtained as a yellow oil. HPLC retention times (gradient program, 254 nm): 12, 3.1 min; 13C, 20.9 min. ¹H-NMR (CDCl₃, 400 MHz) ☐ 7.40 (d, 1H), 6.22 (s, 1H), 5.76 (d, 1H), 5.64 (q, 1H), 4.46 (m, 1H), 4.02 (m, 4H), 3.66 (m, 1H), 2.47 (d, 2H), 2.40 (s, 2H), 1.80 (t, 2H), 1.57 (d, 3H), 1.37 (d, 6H), 1.26 (dd, 6H).

Example 16

Preparation of 8D

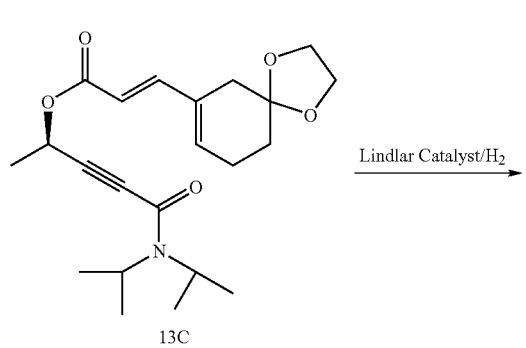

-continued

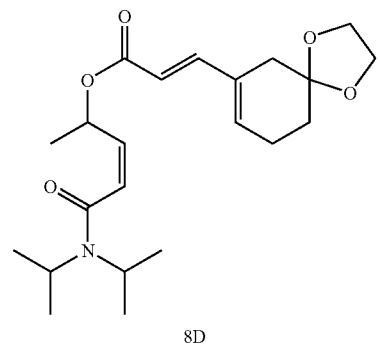

To a slurry of 13C (6.6 g, 17 mmol), quinoline (0.61 mL, 5 mmol) and Lindlar's catalyst (5% Pd/CaCO₃, 0.66 g) in 66 mL of toluene was added hydrogen gas (1 atm, via balloon). The mixture was stirred at room temperature, and monitored at intervals for reaction progress by HPLC. Upon completion of reaction (approximately 3 hours), the mixture was washed with 33 mL of 1 N hydrochloric acid solution to remove quinoline.

Further purification on Biotage flash chromatograph was performed by loading the mixture onto a 40 g silica cartridge, and washing remaining materials forward with 2×15 mL of toluene. Pure fractions were collected after eluting with 500 mL of 30% ethyl acetate in heptane. Upon concentrating, 7.3 g of yellow oil (8D) was obtained (95% yield after subtracting for residual toluene). HPLC retention times (gradient program, 254 nm): toluene, 18.9 min; 8D, 20.3 min; 13C, 20.9 min. ¹H-NMR (CDCl₃, 400 MHz) ☐ 7.34 (d, 1H), 6.17 (m, 1H), 6.09 (d, 1H), 5.79 (m, 1H), 5.75 (s, 1H), 5.72 (dd, 1H), 4.02 (m, 5H), 3.54 (m, 1H), 2.45 (d, 2H), 2.39 (s, 2H), 1.79 (t, 2H), 1.48-1.41 (m, 9H), 1.24 (d, 3H), 1.18 (d, 3H).

Example 17

Preparation 7E

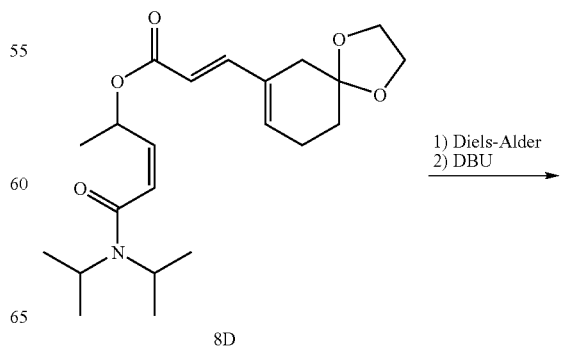

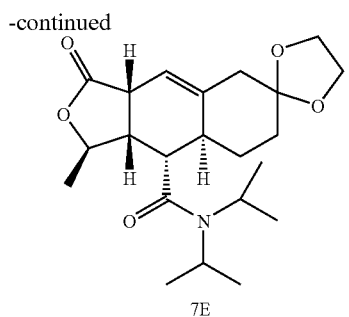

7E

A solution of 8D (2.8 g, 7.2 mmol) in 28 mL of o-xylene in a 100 mL sealed tube was heated at reflux (147° C.) for 16 hours. Upon cooling to below 50° C., 1,8-diazabicyclo[5.4.0]undec-7-ene (0.04 g, 0.3 mmol) was added, and the solution further stirred at 70° C. for 4 hours to complete epimerization. H-NMR (CDCl$_3$, 400 MHz) showed a 98:2 ratio of the exo/endo isomer (from lactone proton signal at δ 4.93 versus 4.65 ppm).

The product was purified via a Biotage flash chromatograph equipped with 90 g silica cartridge. The solution of crude product was directly loaded onto the column, and washed forward with 2×10 mL of toluene. Pure fractions were collected after eluting with 1.5 L of 25% ethanol in toluene. After concentrating on rotovap (40° C., 26 mm Hg), a yellow oil (3.3 g) was obtained (86% yield after subtracting for residual toluene). HPLC retention times (gradient program, 215 nm) □ 7E, 18.3 min. $^1$H-NMR (CDCl$_3$, 400 MHz) □ 5.38 (s, 1H), 4.66 (m, 1H), 3.98 (m, 4H), 3.44 (s, 1H), 3.36 (d, 1H), 2.72 (m, 2H), 2.41 (s, 2H), 2.37 (m, 1H), 1.87 (m, 1H), 1.78 (m, 2H), 1.42 (t, 6H), 1.37 (d, 3H), 1.30 (d, 3H), 1.20 (d, 3H), 1.25-1.17 (m, 2H).

Compound 7E was reduced following the same procedures as described for the conversion of 7B to 7C.

Example 18

Preparation of 22A

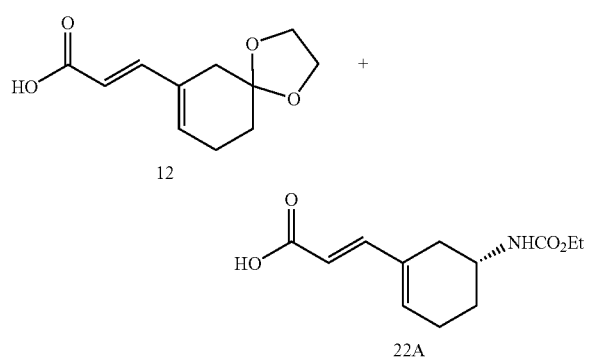

22A

To a 3 L three neck flask equipped with an agitator, thermometer, and a nitrogen inlet, was added 100 g of 12, 1 L of acetonitrile, 600 mL 0.7N p-toluenesulfonic acid aqueous solution. The reaction mixture was agitated at 20° C. for 20 hours before cooling to 0° C. About 40 mL of 50% sodium hydroxide aqueous solution was added to adjust pH to between 7 and 7.5 while maintaining the temperature at 0° C., followed by adding 135 g of ammonium acetate. To the reaction mixture was added 60 g of NaCNBH$_3$ in portions in 4 hours. The resulting mixture was slowly warmed to room temperature and agitated for two days. The temperature was cooled to below 5° C., and pH was adjusted to about 12 with 50% sodium hydroxide aqueous solution. About 250 mL of ethyl chloroformate was then slowly added while maintaining the temperature below 5° C. The pH was then adjusted to 7 with 35% aqueous hydrochloric acid solution. The reaction mixture was concentrated under vacuum to remove acetonitrile and the pH was adjusted to about 2 with 35% aqueous hydrochloric acid solution at below 5° C. Product was extracted with 1 L of ethyl acetate twice. Combined organic layers were washed with water to remove urethane. The organic layer was then concentrated under vacuum, causing the product to precipitate out as crystal. The crystal was filtered and dried to provided 30 g solid of racemic 22A (26% yield). The racemic product was then resolved by preparative chiral HPLC to provide pure Compound 22A. $^1$H-NMR (DMSO-d$_6$) □ 12.1 (brs, 1H), 7.19 (d, J=15.8 Hz, 1H), 7.14 (s, 1H), 6.21 (s, 1H), 5.66 (d, J=15.8 Hz, 1H), 4.00 (q, J=6.80 Hz, 2H), 3.57 (s, 1H), 2.20-2.40 (m, 3H), 1.90-2.00 (m, 1H), 1.78 (m, 1H), 1.43 (m, 1H), 1.19 (t, J=7.05 Hz, 3H).

The preparative chiral HPLC conditions are as follows. Column: ChiralPak AD-H 3.0 cm i.d.×25 cm L; Eluent: CO2/MeOH=75/25; Temperature: 30° C.; Recovery Yield for Compound 22A: 89%; Purity: 98.5% ee.

Example 19

Preparation of 21B

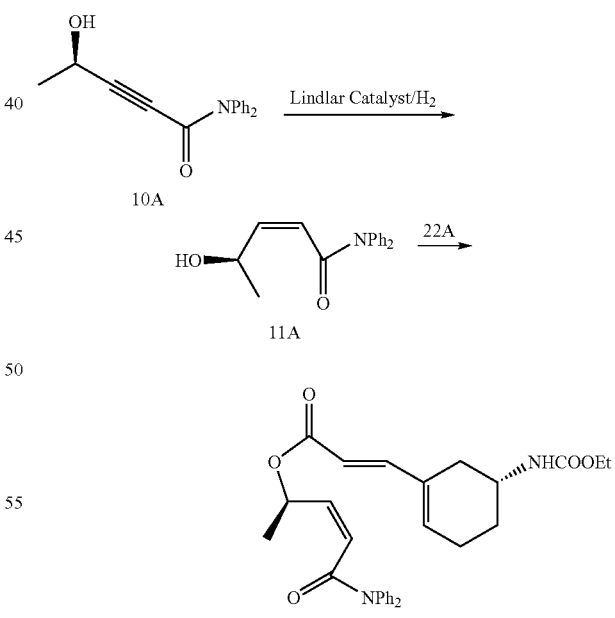

21B

In a procedure analogous to the synthesis of ester 8 via EDCl method, the experiment performed with carbamate acid 22A (1.0 g, 4.2 mmol) gave 0.83 g of 21B (clear oil, 48% yield). $^1$H-NMR (CDCl$_3$, 400 MHz) □ 7.25-7.39 (m, 11H), 6.27 (m, 1H), 6.17 (s, 1H), 5.77-5.91 (m, 3H), 4.68 (s, 1H), 4.15 (m, 2H), 3.94 (s, 1H), 2.57 (d, 1H), 2.33 (m, 1H), 2.01 (m, 1H), 1.94 (m, 1H), 1.61 (m, 2H), 1.49 (d, 3H), 1.28 (t, 3H).

Example 20

Preparation of 20B Via Diels-Alder Reaction

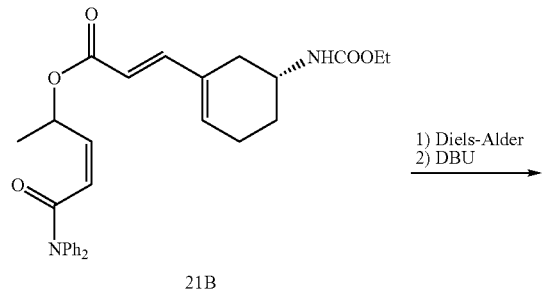

In a procedure analogous to the synthesis of 7B, the experiment performed on 21B (1.80 g, 3.7 mmol) showed a 93:7 ratio of exo/endo isomer by H-NMR. Upon purification via Biotage flash chromatography, 1.2 g of white solid was obtained (66.7% yield). (HPLC retention times (254 nm): endo isomer of 20B, 7.8 min; 20B, 8.0 min; 20 before epimerization, 8.9 min; alkenyl ester, 15.9 min. $^1$H-NMR (CDCl$_3$, 400 MHz) □ 7.23-7.51 (m, 10H), 5.30 (s, 1H), 4.71 (m, 1H), 4.56 (d, 1H), 4.11 (m, 2H), 3.44 (s, 1H), 2.98 (d, 1H), 2.63 (m, 3H), 2.48 (m, 1H), 2.13 (m, 2H), 1.91 (m, 1H), 1.55 (d, 3H), 1.29 (m, 4H), 0.98 (m, 1H).

Example 21

Preparation of 25B Via Hydrogenation

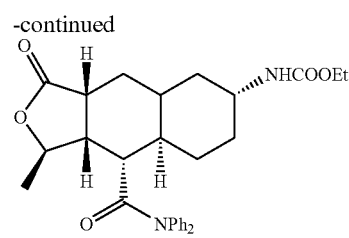

In a procedure analogous to the synthesis of 7C, the experiment performed on 20B (0.52 g, 1.1 mmol) gave 0.47 g of Compound 25B (90% yield). HPLC retention times (isocratic program, 254 nm): 25B, 15.9 min; 20B, 20.0 min. $^1$H-NMR (CD$_3$CN, 400 MHz) □ 7.27-7.50 (m, 10H), 5.39 (d, 1H), 4.83 (m, 1H), 4.01 (m, 2H), 3.37 (m, 1H), 2.01-2.52 (m, 6H), 1.82 (d, 1H), 1.68 (m, 1H), 1.53 (m, 1H), 1.46 (d, 3H), 0.99-1.22 (m, 7H).

Example 22

Conversion of 25B to 17A

To a 250-mL 3-neck flask equipped with an agitator, thermometer, and a reflux condenser, were added 10 g of 25B (20.4 mmol) and THF (50 mL). To this solution was added an aqueous solution of 5% (w/w) sodium hydroxide (50 mL). The reaction mixture was then heated to 40° C. and agitated at 40° C. for about 4 hours. When the hydrolysis reaction was judged complete, toluene (50 mL) was added and the mixture was agitated at a rather fast rate for about 10 minutes. The organic phase containing the by-product was separated from the aqueous phase containing product. The organic phase was back extracted with 5% aqueous NaOH solution (50 mL). The combined aqueous solutions were extracted twice with toluene (2×50 mL) and the organic extracts were discarded. To the aqueous solution were added a solvent mixture of toluene (25 mL) and THF (50 mL). The resulting mixture was cooled to between 0 to 5° C. A 2 N hydrochloric acid aqueous solution (circa 59 mL) was added to adjust the pH of the mixture from about 13 to 2.5 at 0 to 5° C. The aqueous phase was then separated from the organic phase and extracted with a solvent mixture of toluene (25 mL) and THF (50 mL). The organic phase and organic wash were combined and diluted with THF (50 mL). The mixture was then concentrated atmospherically to a final moisture content of <0.05% by repeated distillations. The crude product was used in the next step without further isolation and purification (containing 6.80 g, 99% yield). $^1$H-NMR (CD$_3$CN) □ 9.72 (bs, 1H), 7.17-7.41 (Ph in toluene), 5.45 (bs, 1H), 4.68 (dt, J=5.90, 16.0, 1H), 4.03 (q, J=7.10, 2H), 3.45-3.50 (m, 1H), 2.50-2.65 (m, 2H), 2.45 (dd, J=5.64, 11.5, 1H), 2.36 (methyl in toluene), 1.83 (m, 4H), 1.34-1.50 (qt, J=2.91, 11.0, 1H), 1.32 (d, J=5.91, 3H), 1.15-1.25 (m, 6H), 0.95-1.05 (m, 2H).

Example 23

Preparation of 23C

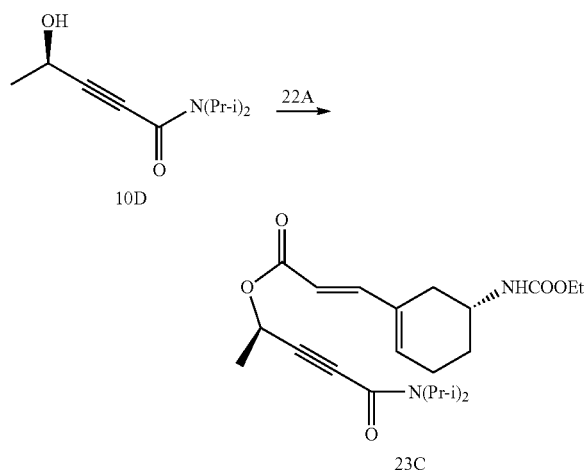

To a solution of 22A (3.0 g, 13 mmol) in 20 mL of toluene was added triethylamine (4.9 mL, 35 mmol), and the resulting slurry was cooled to 0° C. To further solubilize the mixture, 20 mL of tetrahydrofuran was added. Mixed anhydride formation was initiated via addition of trimethylacetyl chloride (1.5 mL, 1.2 mmol) over 5 minutes, and completed through stirring at 0° C. for 2 hours. Catalytic amounts of 4-(dimethylamino)pyridine (0.05 g, 0.4 mmol) and alcohol 10D (2.0 g, 10 mmol) were then added into the brown slurry/mixture, followed by 5 mL of tetrahydrofuran to wash remaining reagents down.

After stirring for 72 hours at 0° C., cooling was removed, and the reaction quenched with 20 mL of water. The lower aqueous layer was separated, while the organic was washed with a mixture of 20 mL saturated sodium bicarbonate solution and 10 mL of water, and then concentrated on rotovap (35° C., 26 mm Hg) to yield 6.5 g of brown oil.

Purification was performed on a Biotage flash chromatograph equipped with 90 g silica cartridge. The crude material was made into a slurry with 10 mL of heptane, loaded onto the column, and washed down with toluene (2×15 mL). Pure fractions were collected after eluting with 1500 mL of 30% ethyl acetate in heptane. Upon concentration, 3.8 g of pale yellow oil (23D) was obtained (91% yield). HPLC retention times (gradient program, 254 nm): 22, 4.2 min; 23C, 20.7 min. $^1$H-NMR (CDCl$_3$, 400 MHz) □ 7.32 (d, 1H), 6.16 (s, 1H), 5.75 (d, 1H), 5.61 (q, 1H), 4.85 (d, 1H), 4.42 (m, 1H), 4.10 (q, 2H), 3.88 (s, 1H), 3.62 (m, 1H), 2.53 (dd, 1H), 2.33 (d, 2H), 2.02 (m, 1H), 1.88 (m, 1H), 1.55 (d, 3H), 1.34 (d, 6H), 122 (m, 9H).

Example 24

Preparation of 21C

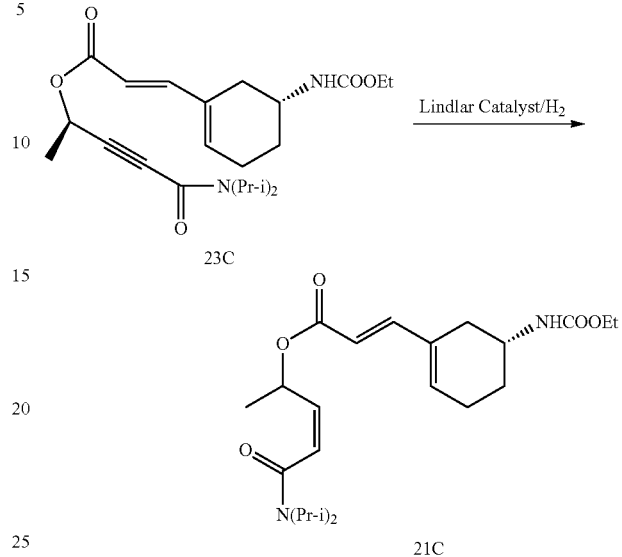

To a slurry of 23C (3.4 g, 8.1 mmol), quinoline (0.31 mL, 2.6 mmol) and Lindlar's catalyst (5% Pd/CaCO$_3$, 0.34-0.85 g) in 34 mL of toluene was added hydrogen gas (1 atm, via balloon). The mixture was stirred at room temperature, and monitored at intervals for reaction progress by HPLC. Upon completion of reaction (<4% of 23C on HPLC analysis), the mixture was filtered to remove catalysts, and 2×15 mL of toluene was used to rinse the remaining materials forward. The filtrate was washed twice with 15 mL of 0.5 N hydrochloric acid solution (to purge quinoline), and then neutralized by further washing with 15 mL of saturated sodium bicarbonate solution and 15 mL of water. The isolated organic was concentrated on rotovap (40° C., 26 mm Hg) to give 3.9 g of yellow oil (88% yield after subtracting for residual toluene). H-NMR analysis showed material to be pure, and hence could be used directly in next synthesis step. HPLC retention times (gradient program, 254 nm): toluene, 18.9 min; 21C, 20.3 min; 23C, 20.7 min. $^1$H-NMR (CDCl$_3$, 400 MHz) □ 7.26 (d, 1H), 6.14 (m, 1H), 6.09 (d, 1H), 5.80-5.70 (m, 3H), 4.72 (d, 1H), 4.13 (m, 2H), 4.01 (m, 1H), 3.94 (s, 1H), 3.53 (m, 1H), 2.58 (dd, 1H), 2.35 (m, 2H), 1.99 (m, 1H), 1.90 (m, 1H), 1.59 (m, 1H), 1.43 (m, 9H), 1.24 (m, 6H), 1.17 (d, 3H).

Example 25

Preparation of 20C

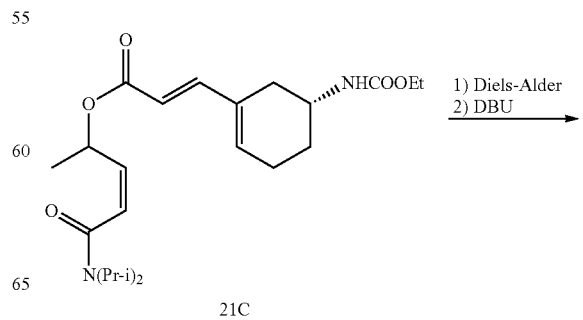

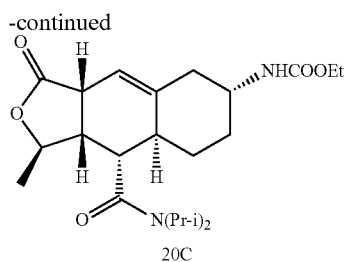

A solution of 21C (3.0 g, 7.1 mmol) in 30 mL of o-xylene in a 100 mL sealed tube was heated at reflux (147° C.) for 21 hours. Upon cooling to room temperature, the mixture was washed twice with 15 mL of saturated sodium bicarbonate solution to purge impurities, and the organic layer was concentrated (50° C., 26 mm Hg) to give 3.7 g of brown oil. This crude product was used directly in subsequent reduction step. H-NMR (CDCl$_3$, 400 MHz) showed a 96:4 ratio of the exo/endo isomer (from alkene proton signal at δ 5.41 versus 5.22 ppm). HPLC retention times (isocratic program, 215 nm): endo isomer of 20C, 10.5 min; 20C, 12.8 min; toluene, 14.0 min; o-xylene, 22.4 min.

Example 26

Preparation of 25C

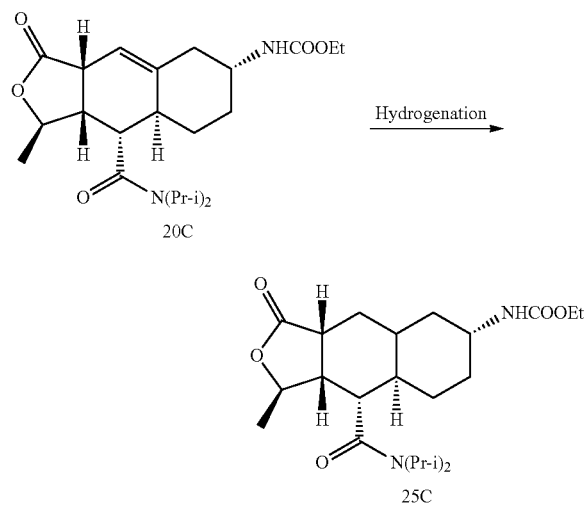

To a slurry of 20C (3.7 g of oil from above procedures) and Pt/C catalyst (5% Pt/C, 50% wet-1.0 g) in 30 mL of ethyl acetate was added hydrogen gas (1 atm, via balloon). The mixture was stirred at room temperature, and monitored at intervals for reaction progress by HPLC. Upon completion of reaction (<3% of 20C on HPLC analysis after 12 hours), the mixture was concentrated to dryness on rotovap (30° C., 26 mm Hg), re-dissolved into a slurry with 10 mL of toluene, and loaded onto a 90 g silica cartridge for purification by Biotage flash chromatography. Some toluene (3×5 mL) was used to wash remaining materials onto the column. Pure fractions were collected after eluting with 1000 mL of 40% ethyl acetate in heptane and 2000 mL of 50% ethyl acetate in heptane. Upon combining and concentrating the desired fractions on rotovap (30 C, 26 mm Hg), 2.5 g of white solid 25C was obtained (83% yield for 2 steps). HPLC retention times (isocratic program, 215 nm): 25C, 10.1 min; 20C, 12.7 min. $^1$H-NMR (CDCl$_3$, 400 MHz) □ 4.81 (m, 1H), 4.71 (d, 1H), 4.09 (m, 2H), 4.00 (m, 1H), 3.46 (m, 2H), 2.61 (m, 1H), 2.48 (q, 1H), 2.20 (m, 1H), 2.04-1.79 (m, 4H), 1.60 (m, 1H), 1.42 (d, 3H), 1.38 (d, 3H), 1.34 (d, 3H), 1.29-1.16 (m, 10H), 0.93 (m, 1H).

Example 27

Preparation of Compound 28A

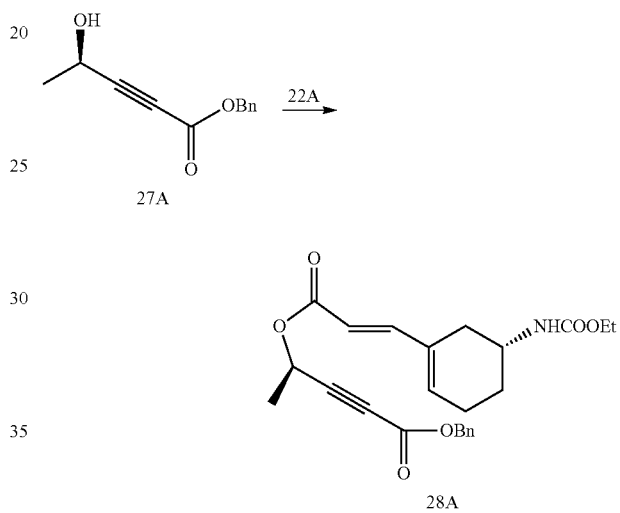

To a 100 mL three neck flask equipped with an agitator, thermometer, and a nitrogen inlet, was added 22A (2.0 g) and tetrahydrofuran (50 mL). The mixture was agitated for 10 minutes and then triethylamine (4 mL) was added slowly at below 25° C. The mixture was cooled to 0° C. followed by slowly adding trimethylacetyl chloride (1 mL) while maintaining the temperature below 5° C. After the reaction mixture was agitated for 30 minutes at below 5° C., 4-(dimethylamino)pyridine (40 mg) and 27A (1.7 g active) were added. The resulting mixture was agitated at below 5° C. After the reaction was judged complete, water (5 mL) was added slowly to quench the reaction and the temperature was allowed to warm up to 20° C. 5% sodium bicarbonate aqueous solution (20 mL) and ethyl acetate (50 mL) were added. Organic layer was separated and concentrated under vacuum to provide crude oil. The oil was further purified by column chromatography to provide about 2.0 g of Compound 28A as white solid (56% molar yield). $^1$H-NMR (DMSO-d$_6$) □ 7.40 (s, 5H), 7.32 (d, J=15.8 Hz, 1H), 7.15 (d, J=7.29 Hz, 1H), 6.33 (s, 1H), 5.76 (d, J=15.8 Hz, 1H), 5.60 (q, 6.76 Hz, 1H), 5.20 (s, 2H), 3.98 (q, J=7.08 Hz, 2H), 3.57 (s, 1H), 2.42 (d, J=16.9 Hz, 1H), 2.30 (s, 2H), 1.85-2.00 (m, 1H), 1.76-1.80 (m, 1H), 1.51 (d, J=6.82 Hz, 3H), 1.43 (m, 1H), 1.16 (t, J=7.09 Hz, 3H).

Example 28

Preparation of 17A

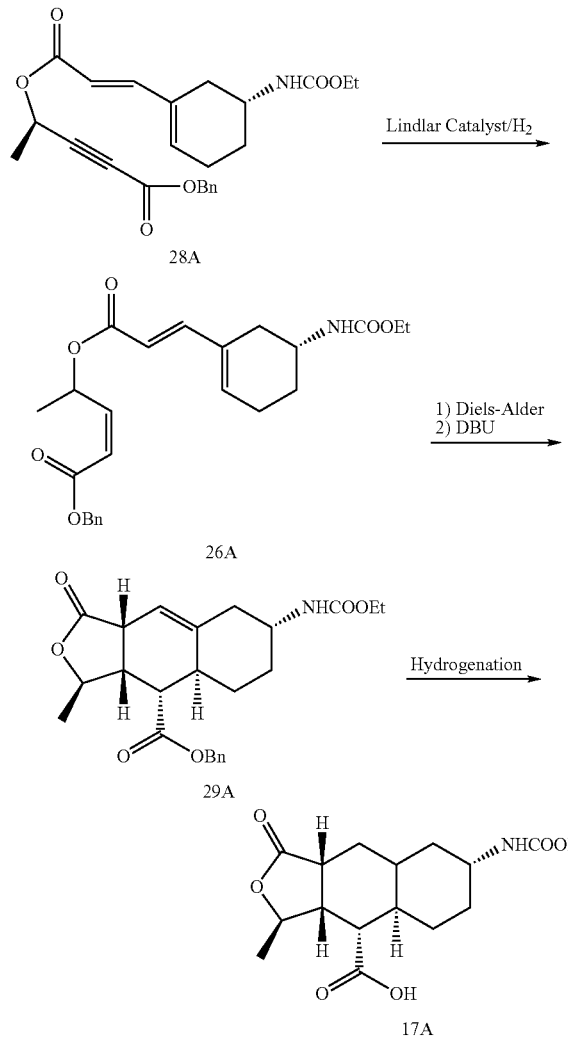

To a 100 mL three neck flask equipped with an agitator, thermometer, and a nitrogen inlet, were added Compound 28A (0.5 g), Lindlar catalyst (50 mg), tetrahydrofuran (20 mL), and quinoline (0.1 mL). The mixture was agitated under hydrogen (15 psig) at room temperature for about 15 minutes. The reaction mixture was diluted with ethyl acetate (50 mL0 before filtering through Celite to remove catalyst. The organic solution was washed with 1N hydrochloric acid aqueous solution (10 mL) to quinoline, and then washed with 5% sodium carbonate aqueous solution (10 mL), and brine (10 mL). The organic layer was concentrated to give crude 26A as an oil.

Without further purification, the oil was dissolved in o-xylene (4 mL) to make solution A. To the second 100 mL three neck flask equipped with an agitator, thermometer, condenser, and a nitrogen inlet, was added o-xylene (3 mL). The solvent was heated to reflux at 140° C. followed by slowly adding the solution A through syringe pump in about 1 hour. The mixture was agitated at reflux for an additional 6 hours and then cooled to room temperature. 1,8-Diazabicyclo[5.4.0]undec-7-ene (1 drop) was added, and the resulting mixture was agitated at room temperature for about 12 hours. The mixture was diluted with ethyl acetate (25 mL), washed with 1 N hydrochloric acid aqueous solution (5 mL), 5% sodium bicarbonate aqueous solution (5 mL), and brine (5 mL). The organic layer was concentrated to give crude 29A as an oil.

Without purification, the crude 29A was dissolved in ethyl acetate (25 mL). 5 mL of the solution was diluted with ethyl acetate (15 mL) and then transferred into a hydrogenator together with 50 mg of 5% Pt/C (50% wet). The resulting mixture was agitated under hydrogen (100 psig) at room temperature for 20 hours. Another 10 mg of 10% Pd/C (50% wet) was added and the mixture was agitated under hydrogen (100 psig) at room temperature for another 2 hours. After filtering through Celite, the mixture was concentrated under vacuum to provide about 35 mg of crude 17A. $^1$H-NMR (CD$_3$CN-d$_6$) □ 9.30 (brs, 1H), 5.40 (s, 1H), 4.69 (m, 1H), 4.03 (q, J=7.00 Hz, 2H), 3.40 (m, 1H), 2.55-2.66 (m, 2H), 2.42 (dd, J=11.5, 5.67 Hz, 1H), 1.78-1.95 (m, 4H), 1.35 (m, 1H), 1.30 (d, J=5.91 Hz, 3H), 1.18-1.27 (m, 6H), 0.95-1.05 (m, 1H).

While the present invention has been described in conjunction with the specific embodiments set forth above, many alternatives, modifications and variations thereof will be apparent to those of ordinary skill in the art. All such alternatives, modifications, and variations are intended to fall within the spirit and scope of the present invention.

What is claimed is:

1. A process for preparing Compound 3A:

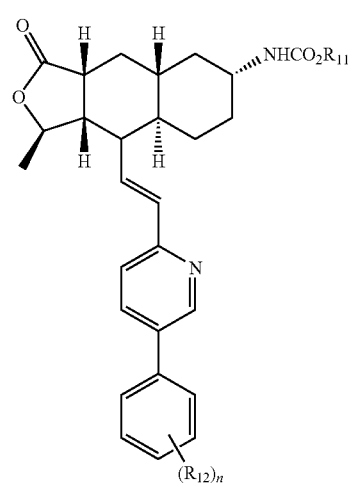

wherein $R_{11}$ is unsubstituted alkyl, $R_{12}$ is halogen, and n is 1, comprising:

(a) reducing Compound 7

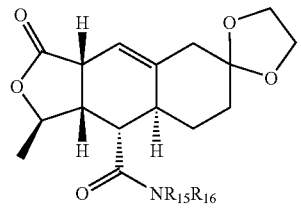

to Compound 7A':

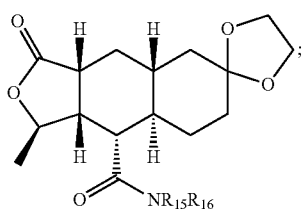

wherein $R_{15}$ and $R_{16}$ are each independently selected from the group consisting of H, unsubstituted alkyl or phenyl, or, when taken together with the nitrogen to which they are attached, form a morpholine ring;

(b) hydrolyzing Compound 7A' to yield Compound 15:

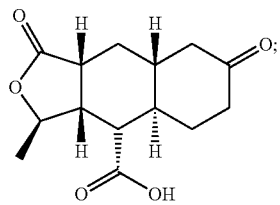

(c) aminating Compound 15 to yield Compound 4:

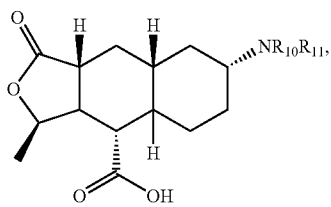

wherein $R_{10}$ and $R_{11}$ are H;

(d) converting Compound 4 to Compound 17:

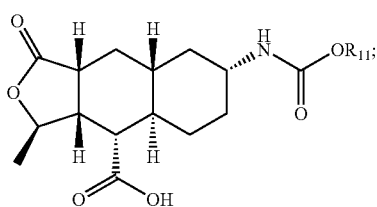

(e) converting Compound 17 to Compound 18:

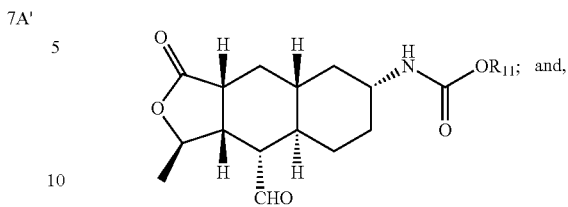

(f) converting Compound 18 to Compound 3A:

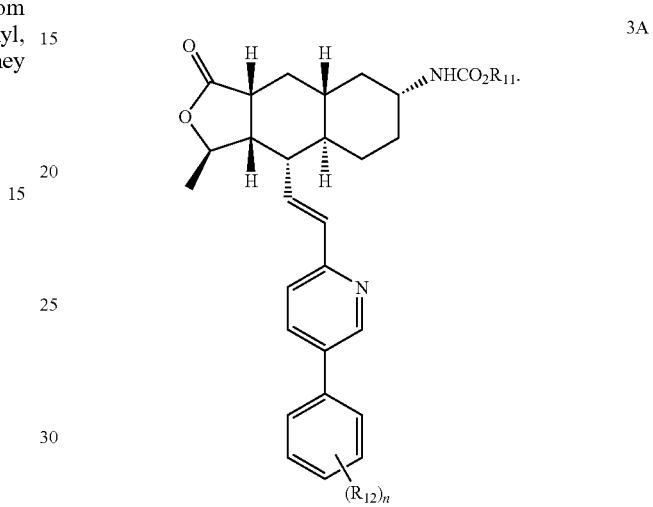

2. The process of claim 1, wherein the step of converting Compound 18 to Compound 3A comprises reacting Compound 18 with Compound 6:

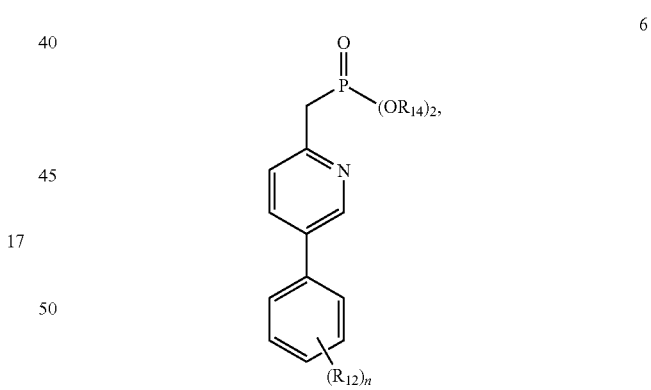

wherein $R_{14}$ is unsubstituted alkyl to yield Compound 3A.

* * * * *